United States Patent [19]

Garnett

[11] Patent Number: 5,776,973

[45] Date of Patent: Jul. 7, 1998

[54] PALLADIUM COMPLEXES AND METHODS FOR USING SAME IN THE TREATMENT OF PSORIASIS

[76] Inventor: Merrill Garnett, 178 W. Main St., East Islip, N.Y. 11730

[21] Appl. No.: 544,458

[22] Filed: Oct. 18, 1995

Related U.S. Application Data

[62] Division of Ser. No. 157,570, Nov. 26, 1993, Pat. No. 5,463,093.
[51] Int. Cl.$^6$ .................................................. A01N 43/26
[52] U.S. Cl. ........................ 514/440; 514/557; 514/558; 514/559; 514/863; 554/102
[58] Field of Search ........................... 584/102; 514/440, 514/857, 858, 859, 863

[56] References Cited

PUBLICATIONS

P. Reichard, From RNA to DNA, Why so Many Ribonuclease Reductases? *Science* 260:1773–1777 (1993).

J.A. Hamilton et al., Cobamides and Ribonucleotide Reduction. VII. Cobalt(III)alamin as a Sensitive Probe for the Active Center of Ribonucleotide Reductase, *Biochemistry* 10(2):347–355 (1971).

A.I. McMullen, The Electrostatic Free Energy of Macromolecular Systems, *Electronic Aspects of Biochemistry, Annals of the New York Academy of Sciences* 158: 223–239 (1969).

M.D. Purugganan, Accelerated Electron Transfer Between Metal Complexes Mediated by DNA, *Science* 241:1645–1649 (1988).

C. Abate et al., Redox Regulation of Fos and Jun DNA—Binding Activity in Vitro, *Science* 249: 1157–1161 (1991).

S.Y. Shaw et al., Knotting of a DNA Chain During Ring Closure, *Science* 260: 533–536 (1993).

P.N. Campbell et al., *Biochemistry Illustrated* 2nd ed., Churchill Livingstone, Edinburgh, London, Melbourne and New York 1988, p. 126.

N. Hadjiliadis, Interaction of Thiamine and its Phosphate Esters with Pt (II) and Pd(II), *Inorganic Chimica Acta* 25:21–31 (1977).

L. Manuelidis, A View of Interphase Chromosomes, *Science* 250: 1533–1540 (1990).

J.J. Yunis et al., Heterochromatin, Satellite DNA, and Cell Function, *Science*, 174: 1200–1208 (1971).

G.J. Shugra et al., *The Chemist's Ready Reference Handbook*, McGraw–Hill, New York, p. 6.19 (1990).

M. St.C. Flett, *Physical Aids to the Organic Chemist*, Elsevier, Amsterdam—New York pp. 162–163 (1962).

L. Schotte, Spectrochemical Studies on Disulphides I. An Investigation of Some Linear and Cyclic Carboxylic Substituted Disulphides With Special Reference to the 1.2–Diothiolane System, *Ark. Kemi* 8 (56): 579–596 (1955).

L. Schotte, Studies on Sulphur Compounds Related to Glutaric and Pimelic Acid With Special Reference to the 1,2–Dithiolane System, *Ark. Kemi*, 9 (37): 441–469 (1956).

L. Schotte, Spectrochemical Studies on Disulphides IV. The Structure of Same Polysulphides, *Ark. Kemi* 9 (29): 361–376 (1956).

J.I. Maloy, Factors Affecting the Shape of Current–Potential Curves, *Journal of Chem. Ed.* 60(4): 285–289 (1983).

R.G. Finke et al., Radical Cage Effects in Coenzyme $B_{12}$: Radical Trapping, Product and Kinetic Studies, *J. Inorg. Biochem.* 51(1 and 2): 221 (1993).

R. Witkus, Stiensma et al., Berbee et al., Yeast Biology, *Science* 257: 1610 (1992).

*Primary Examiner*—Deborah D. Carr
*Attorney, Agent, or Firm*—Hoffmann & Baron

[57] ABSTRACT

Novel palladium complexes and pharmaceutical compositions comprising the same are provided. Such complexes comprise (palladium)$_m$(lipoic acid)$_n$, wherein m and n are each independently 1 or 2. A process for preparing such complexes is also disclosed. In addition, a method of treatment of tumors and a method of treatment of psoriasis comprising administering the pharmaceutical compositions of the present invention are provided.

10 Claims, 35 Drawing Sheets

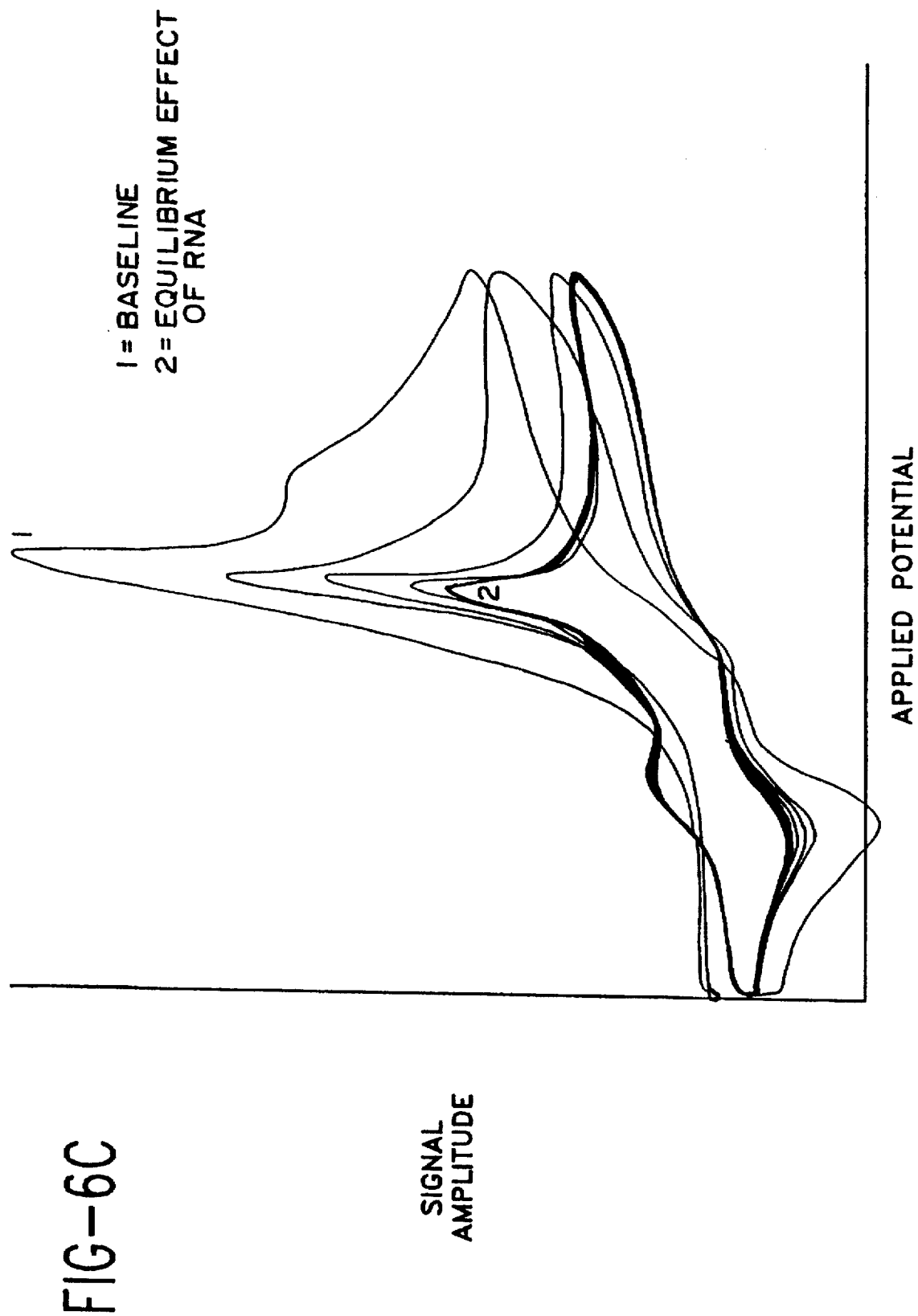

FIG-11A
FIG-11B

5,776,973

PALLADIUM COMPLEXES AND METHODS FOR USING SAME IN THE TREATMENT OF PSORIASIS

This is a divisional of application Ser. No. 08/157,570 filed on Nov. 26, 1993, now U.S. Pat. No. 5,463,093.

BACKGROUND OF THE INVENTION

1. Field of the Invention

The present invention relates generally to novel palladium complexes and pharmaceutical compositions comprising same. In addition, a method for the preparation of novel palladium complexes is disclosed. Also disclosed is a method for the treatment of tumors comprising administering the novel palladium complexes of the present invention and a method for the treatment of psoriasis comprising administering the novel palladium complexes of the present invention.

2. Related Art

A number of researchers have studied the role that nucleic acids play in tumorigenesis. Although electron reduction of single nucleotides have been reported in, for example, Reichard, "From RNA to DNA, Why So Many Ribonucleotide Reductases?" *Science* 260:1773–1777 (Jun. 18, 1993); and Hamilton et al., "Cobamides and Ribonucleotide Reduction VII Cobalt(II)alamin as a Sensitive Probe for the Active Center of Ribonucleotide Reductase," *Biochemistry* 10(2) :347–355 (1971), previous reviews of nucleic acids and their role in tumorigenesis make no mention of reactions or substances which result in the electron reduction of DNA or RNA. Townsend et al. (ed), *Nucleic Acid Chemistry, Part 3*, Wiley Interscience, New York (1986); Saenger, *Principles of Nucleic Acid Structure*, Springer-Verlag, New York (1984); Walker, "Nucleic Acids," *Methods in Molecular Biology*, vol. 2, Humana Press, Clifton, N.J. (1984); Grossman et al. (ed), "Nucleic Acids—part 1," *Methods in Enzymology*, vol. 65, Academic Press, New York (1980); Fasman (ed), "Nucleic Acids," *Handbook of Biochemistry and Molecular Biology* (3d), vol. 1, CRC Press, Cleveland, Ohio (1975); Blackburn et al. (ed), *Nucleic Acids in Chemistry and Biology*, IRL Press, Oxford Univ. Press (1990).

The prevailing view of tumorigenesis today is that it may be treated by site-specific regulation, such as by a repressor protein, at proto-oncogene sites. Such proto-oncogene sites are different for each type of tumor being treated and an extensive effort is required in order to pursue this method of treatment for an individual patient.

In 1969 McMullen described a model of the electrostatic free energy of nucleic acids. McMullen, "The Electrostatic Free Energy of Macromolecular Systems," *Electronic Aspects of Biochemistry*, Annals NY Acad. Sci., Vol. 158, Art. 1, 223–239 (May 1969). Purugganan et al. in 1988 described the electron energy interactions of DNA. Purugganan et al., "Accelerated Electron Transfer Between Metal Complexes Mediated by DNA," *Science* 241:1645–1649 (Sep. 23, 1988).

The first redox regulation of the transcription of the proto-oncogenes c-fos and c-jun was reported in 1990 in a landmark paper by Abate et al., "Redox Regulation of Fos and Jun DNA-Binding Activity in Vitro," *Science* 249:1157–1161 (Sep. 7, 1990). Abate et al. had previously identified a nuclear factor that stimulates the DNA-binding activity of fos and jun in vitro. This factor did not bind to the fos-jun complex or to the DNA regulatory element known as the activator protein-1 (AP-1) binding site, thereby suggesting that it regulated DNA-binding activity indirectly. The authors hypothesized that the nuclear factor reduces a critical cysteine residue in fos and jun that is required for DNA-binding activity. It was believed that one or more cysteine residues in fos and jun are important for DNA binding and that reduction is required for association with DNA. Abate et al. at 1158. The findings of Abate et al. thus suggested that modification of the redox state of fos and jun may contribute to the formation of specific protein-DNA complexes. The bacterial transcriptional regulatory protein, Oxy R, which regulates gene expression in response to oxidative stress, was found to change DNA-binding specificity depending on the redox state. Thus, regulation by reduction-oxidation was believed to be a mechanism of control for certain transcription factors.

Recently, Shaw et al. studied the free energy of formation of relaxed trefoil and figure-eight DNA knots. Supercoiled trefoil DNA knots were also evaluated. The authors found that the presence of a knot in a relaxed or supercoiled DNA ring is associated with a substantial free energy cost. Furthermore, in enzyme-catalyzed reactions that yield knotted products, this free energy cost must be compensated for by a favorable free energy term, such as that derived from protein-DNA interactions. Shaw et al., "Knotting of a DNA Chain During Ring Closure," *Science* 260:533–536 (Apr. 23, 1993).

In spite of the above-described research relating to tumorigenesis to date, the conventional methods for the treatment of tumors in individual patients have not met with resounding success. Thus, the search for a new method or methods for the treatment of tumors continues. Likewise, there are other disease states and conditions, such as psoriasis, which have long sought a safe and effective method of treatment.

BRIEF DESCRIPTION OF THE DRAWINGS

In FIGS. 2D and 2E, the concentration is 0.00012M. In FIG. 2D, the spectrum is ended at 400.0 nm and 0.542 A, and a reference peak is at 289.0 nm and 0.75 A. In FIG. 2E, the spectrum is ended at 550.0 nm and 0.036 A, and a reference peak is at 396.0 nm and 0.553 A. FIG. 2F illustrates the absorbance spectra of Pd-lipoic acid complexes at varying ratios of palladium to lipoic acid at a Pd concentration of $5 \times 10^{-5}$M. The ratios are 1 Pd:1 lipoic=n 1, 1 Pd:2 lipoic=n 2, and 1 Pd:3 lipoic=n 3.

In FIG. 4A to 7B, the scan direction is (−+) and the scan rate is 100 mV/SEC.

FIGS. 4A, 4B, 4C and 4D illustrate cyclic voltammetric scans of Poly-RC and Poly-R2. FIG. 4A shows the electrochemical signature of a solution of Poly RC in acetate buffer, PLC: 250 µl/0.12M, in a scan from 0 to −1.0 volts at 20 µA sensitivity in an experiment dated Feb. 23, 1993. FIG. 4B shows a solution of 0.3 ml Poly-R2 (0.08M) in scan from 0 to −1.0 volts at 100 µA sensitivity in an experiment date Mar. 16, 1993. FIG. 4C shows a solution of 0.3 ml Poly-R2 (0.08M) in scan from −0.3 to −1.0 volts at 20 µA sensitivity in an experiment dated Mar. 16, 1993. FIG. 4D is a comparison of signals of Poly-RC and Poly-R2. FIG. 4E shows the signature of $B_{12}$Ac-Poly-R2 in acetate buffer solution 0.6 ml/0.04M in a scan from 0.03 to −1.0 volts at 20 µA sensitivity in an experiment dated May 19, 1993. FIG. 4F shows the signature of $B_{12}$Ac-Poly R2 in acetate buffer solution, 0.6 ml/0.04M in a scan from 0 to −1.0 volts at 20 µA sensitivity in an experiment dated May 19, 1993.

FIG. 5 shows the charge interaction of Poly-RC in a solution of 250 µl/0.12M plus DNA (CT) in a solution of 1.0 ml cf 5 mg/ml in a scan from 0 to −1.0 volts at 20 µA sensitivity in an experiment dated Feb. 23, 1993. FIG. 5 shows DNA oxidizes Poly-RC.

FIG. 6A shows a solution of 0.3 ml Poly R2 (0.08M) plus 1.0 ml DNA 5 mg/ml in a scan from 0 to −1.0 volts at 100 µA sensitivity in an experiment dated Mar. 16, 1993. FIG. 6A shows DNA oxidizes Poly-R2. FIG. 6B shows an acetate buffer solution of 0.3 ml Poly-R2 (0.08M) plus 1.0 ml DNA (CT) 5 mg/ml in a scan from −0.3 to −1.0 volts at 20 µA sensitivity in an experiment dated Mar. 18, 1993. FIG. 6B shows DNA oxidizes Poly-R2. FIG. 6C shows a cyclic voltammetry pattern of the reaction of Poly-R2 and yeast RNA. FIG. 6C shows a solution of Poly-R2 plus RNA in a scan from −0.3 to −1.0 volts at 20 µA sensitivity in an experiment dated Mar. 30, 1993.

FIG. 7A shows aL solution of Poly-R2 (0.3 ml: 0.08M) plus DNA (1.0 ml: 5 mg/ml) plus $B_{12}$ (1.0 ml: 0.2 mg/ml) in a scan from −0.3 to −1.0 volts at 20 µA sensitivity in an experiment dated Mar. 31, 1993. FIG. 7A shows $B_{12}$ induces a second and further oxidation of Poly-R2 after the DNA. FIG. 7B illustrates a cyclic voltammetry pattern of the reaction of the activated $B_{12}$-Poly-R2 complex and DNA. FIG. 7B shows a solution of (1) $B_{12}$AC-Poly R (0.6 ml/0.04M) and (2) DNA (CT) 0.5 ml (5 mg/ml) in a scan from −0.3 to −1.0 at 20 µA sensitivity in an experiment dated May 19, 1993. FIG. 7B shows rapid achievement of equilibrium.

FIGS. 10A, 10B, 10C, 11A, 11B, 12A, 12B, 12C, 13A and 13B are clinical photographs taken of patients being treated for psoriasis with $B_{12}$AC-Poly-R2.

FIG. 10A shows R anterolateral abdomen with psoriasis to compare treated areas (R side of photo) with untreated areas (L side of photo). R side has been treated with Polyredox applied once daily for 7 days. Psoriatic lesions appear less scaly, less thick and smooth stretch marks of surrounding and underlying skin are more visible through thinner plaques. Untreated areas on L side remain with thick, scaly, psoriatic lesions. FIG. 10B shows an untreated psoriatic plaque, close up, showing thick, silvery scales with underlying red inflamed base. FIG. 10C shows an area of abdomen treated with Polyredox applied once daily for 7 days. Already there is less scaling and obvious smoothening of lesions. Normal skin markings are visible through the thinner plaques. Redness is from the stain of the compound.

FIG. 11A shows L lateral thigh with psoriasis before treatment: thick papulosquamous plaques showing silvery scales and red inflamed base. FIG. 11B shows L lateral thigh with psoriasis area on L side of photo treated with Polyredox twice daily for 7 days. Treated area appears smoother and thinner.

FIG. 12A shows L lateral thigh with psoriatic plaque before treatment. FIG. 12B shows the same lesion treated with Polyredox twice daily for 2 weeks. Lesion appears flatter and contracted centrally with overall diminution in size. There is overlying yellowish "scab" giving an impression of dryness. Superficial fissuring may signify the drying effect and/or contraction of sections of the lesion. Smaller lesion at 2 o'clock remains unchanged. FIG. 12C shows the same as FIG. 12B at higher magnification. Features mentioned above appear more obvious. Small lesion at 10 o'clock is superficially eroded and appears necrotic.

FIG. 13A shows forearms, dorsolateral view, encased in thick plaques of psoriasis prior to treatment with Polyredox. FIG. 13B shows the same forearms one week later. The L forearm was treated with Polyredox applied 2× daily for 7 days. The R forearm is untreated. Treated areas on the L forearm show less scaling, smoothening and thinning of lesions. Improvement is specially noted on the area below the L elbow (compare with FIG. 13A).

OBJECTS AND SUMMARY OF THE INVENTION

Figure 1:
FIG. 1 shows crystallographic studies of the Pd-lipoic acid complex. The figure shows the trigonal prism of palladium-lipoic acid complex (Poly-RC).

The present inventor has taken a different approach to the treatment of tumorigenesis from those of the prior art. Surprisingly, it has been discovered that by altering the enzymatic or catalytic pathway represented by even a singular or very few gene sites, the native conformation of large tracts of DNA can be altered. The present inventor believes that electron energy from a normal metabolic hydrogen carrier, such as lipoic acid, can be shunted to nucleic acids. The electron energy which is shunted can be measured by conventional voltammetric means.

An object of the present invention is to provide a novel polynucleotide reductase which is a complex comprising palladium or a salt thereof, and lipoic acid or a derivative thereof. The complex may comprise the formula (palladium)$_m$(lipoic acid)$_n$ wherein m and n are each independently 1 or 2.

It is also an object of the present invention to provide a complex for administration to a patient wherein the palladium-lipoic acid complex is present in an amount sufficient to obtain a concentration of at least about 0.01M. The palladium-lipoic acid complex is preferably present in a dispersion or solution.

It is a further object of the present invention to provide a thiamine salt of a palladium-lipoic acid complex composition wherein the palladium, lipoic acid and thiamine are present in a solution at a pH such that a complex is formed.

It is a still further object of the present invention to provide a complex comprising palladium-lipoic acid, which further comprises the addition of other ligands to the palladium-lipoic acid complex.

Another object of the present invention is to provide a thiamine salt of a palladium-lipoic acid complex which further comprises a synthetic cofactor of vitamin $B_{12}$ (cyanocobalamin).

Additionally, the present invention relates to a method of synthesizing a palladium-lipoic acid complex.

It is a further object of the present invention to provide a pharmaceutical composition of matter comprising a pharmaceutically effective amount of a complex of palladium or a salt thereof to treat a tumor or psoriasis, and lipoic acid or a derivative thereof, and a pharmaceutically acceptable carrier therefor. Further, a pharmaceutical composition of matter comprising a palladium-lipoic acid complex which also comprises thiamine or a salt thereof is provided. In addition, a pharmaceutical composition of matter comprising a palladium-lipoic acid-thiamine complex which further comprises as a synthetic cofactor vitamin $B_{12}$ (cyanocobalamin) is provided.

The present invention also relates to a method of treatment of tumors comprising administering the pharmaceutical composition of matter comprising a complex of palladium or a salt thereof and lipoic acid or a derivative thereof in an amount effective for tumor reduction to a patient, e.g., human, in need of such treatment. A further method of treatment of tumors comprises administering a palladium-lipoic acid complex which also comprises thiamine or a salt thereof in an amount effective for tumor reduction to a patient in need of such treatment. In addition, a method of treatment of tumors comprising administering a palladium-lipoic acid-thiamine complex which comprises a synthetic cofactor of vitamin $B_{12}$ (cyanocobalamin) in an amount effective for tumor reduction to a patient in need of such treatment is provided.

In addition, the present invention relates to a method of treatment of psoriasis comprising administering the pharmaceutical composition of matter comprising a complex of palladium or a salt thereof and lipoic acid or a derivative thereof in an amount effective for reduction of maculopapules associated with psoriasis to a patient in need of such treatment. A further method of treatment of psoriasis comprises administering a palladium-lipoic acid complex which also comprises thiamine or a salt thereof in an amount effective for reduction of maculopapules associated with psoriasis to a patient in need of such treatment. In addition, a method of treatment of psoriasis comprising administering a palladium-lipoic acid-thiamine complex which comprises a synthetic cofactor of vitamin $B_{12}$ (cyanocobalamin) in an amount effective for reduction of maculopapules associated with psoriasis to a patient in need of such treatment is provided.

DESCRIPTION OF THE PREFERRED EMBODIMENTS

As previously stated, the present invention relates to the transfer of electron energy from a normal metabolic hydrogen carrier to nucleic acids. As used in the present specification, the term "polynucleotide reductase" is a compound which is capable of shunting electron energy from itself to nucleic acids. In the terminology of organic chemistry, the reductases are "sources" which are able to donate electrons into the nucleic acid "sinks". Scudder, *Electron Flow in Organic Chemistry*, John Wiley, 2–3 (1992). DNA has previously been described as an intermediate for electron transfer reactions in Purugganan et al., which reported that a double-stranded DNA polymer can mediate long-range electron transfer between bound donor-acceptor pairs.

The present inventor has found that a palladium-lipoic acid complex of the present invention can function as a polynucleotide reductase to transfer electrons into DNA and RNA. Further, and without wishing to be bound by any theory, the present inventor believes that when the electron energy from a palladium-lipoic acid complex of the present invention is shunted to DNA or RNA, it alters the nucleic acid configuration. A polynucleotide reductase capable of shunting electron energy from itself to DNA is termed a DNA reductase, while a polynucleotide reductase capable of shunting electron energy from itself to RNA is termed a RNA reductase.

The present inventor has discovered a novel palladium-lipoic acid complex. The complex may exist in a solid form, however, the complex is preferably in a liquid form as a dispersion, or more preferably as a solution. The complex, also referred to as a coordination compound herein, is a compound containing a metal atom or ion bonded by at least one ionic bond to a number of anions or molecules.. The complexes of the present invention comprising a transition metal ion are thermodynamically stable.

As is common in metal to ligand syntheses, multiple complexes of palladium with lipoic acid may be produced. The general formula of the complex of the present invention is $(\text{palladium})_m(\text{lipoic acid})_n$, wherein m and n are each independently 1 or 2. Preferably, m is 1 and n is 1. At least two forms of the Pd-lipoic acid complex have been identified by spectroscopy. These two forms of the Pd-lipoic acid complex are as follows: (1) a 1:1 (n=1) ratio of palladium to lipoic acid, and (2) a 1:2 (n=2) ratio of palladium to lipoic acid. The structure of each of these complexes is as follows:

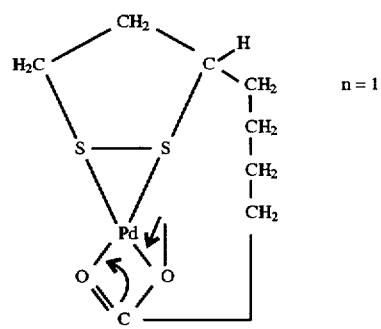

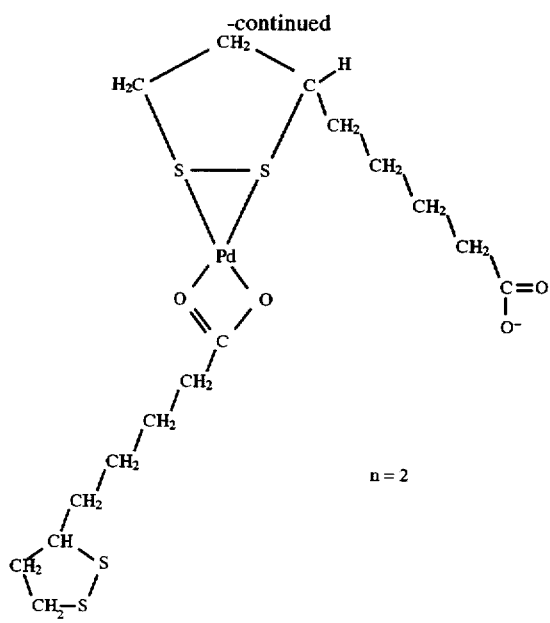

n = 2

The bonds of the palladium-lipoic acid complex are coordinate covalent. More specifically, studies have shown that the palladium-lipoic complex is bonded by coordinate covalent bonds: (1) at the carbonyl end of the substituent having a carboxyl group with probable resonance involvement of both oxygens, and (2) at one or more sulfur atoms. The lipoic acid in the complex comprises a bent carbon chain with the ends of the chain bonded to the palladium. This 1:1 structure is represented above as a bent cyclic structure. However, while the figure shows a planar structure, crystallographic studies as discussed below show the structure to be three-dimensional with the palladium in the center of the complex.

As previously stated, lipoic acid is one component of the complex of the present invention. The present inventor has found that lipoic acid and its derivatives are highly specific for transferring electron energy from a normal metabolic hydrogen carrier to nucleic acids. Lipoic acid occurs in an oxidized or disulfide form, or in a reduced or dithiol form. The structure of lipoic acid in its oxidized form is as follows:

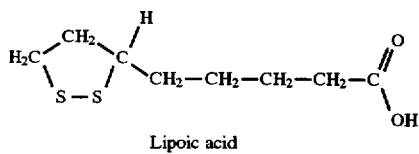

Lipoic acid

The structure of the reduced form of lipoic acid, i.e., dihydrolipoic acid, is as follows:

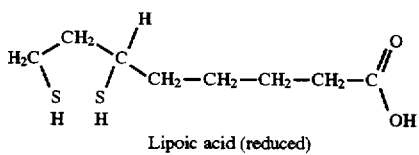

Lipoic acid (reduced)

As can be seen by the above structures, lipoic acid has a long, flexible side chain, which enables it to rotate from one active site to another in enzyme complexes. As shown in Campbell et al., *Biochemistry Illustrated*, 2d, Churchill Livingstone, 126 (1988), lipoic acid is a hydrogen carrier and an acetyl-group carrier for the decarboxylation of pyruvic acid. Lipoic acid is then present as acetyllipoic acid, having both an acetyl group and a hydrogen atom. In the pyruvic decarboxylation reaction, the acetyl group is donated to CoA and the H is donated to $NAD^+$.

Derivatives of lipoic acid, in either, its oxidized or reduced form, may also be used in the practice of the present invention, including lipoic acid analogues having a shortened or lengthened carbon chain, e.g., the lipoic acid derivative may comprise a carbon chain of at least 2 carbon atoms, preferably a $C_2$ to $C_{20}$ hydrocarbon chain, and most preferably a $C_4$ to $C_{10}$ hydrocarbon chain. Lipoic acid derivatives having one to three additional side groups, e.g., carboxyl, sulfur or amine groups, may also be used. The side groups may be attached, for example, to one of the sulfur atoms, along the carbon chain, or may be substituted for the hydroxyl group at the carbonyl end of the lipoic acid moiety. A particularly preferred lipoic acid derivative is, for example, lipoamide.

In addition, the palladium-lipoic acid complex of the present invention may further comprise at least one ligand to the palladium-lipoic acid complex. For example, the additional ligand to the palladium-lipoic acid complex may be an inorganic anionic ligand, including without limitation acetate, acetylacetonate, amine, ammonium chloride, ammonium nitrate, bromide, chloride, fluoride, iodide, nitrate, nitrite, oxalate, oxide, pyridine, sulfate and sulfide. The lipoic acid derivative may further comprise additional cations, for example, sodium, potassium, magnesium, calcium, ammonia, vanadate, molybdate, zinc and tin. Furthermore, the lipoic acid of the complex of the present invention may be present in its reduced or oxidized form. Other derivatives of lipoic acid known in the art may also be used in the practice of the present invention. The derivatives are suitable if the ability to transfer electron energy from a normal hydrogen carrier to a nucleic acid is retained. As used in the present specification, the term "lipoic acid" is intended to include the derivatives specifically identified supra as well as other derivatives known in the art. The features of lipoic acid believed to be necessary for the present invention include at least two sulfur atoms, a hydrocarbon chain having a length of two to twenty carbon atoms, and one or more carboxyl groups.

The metal ion of the novel complex of the present invention is palladium. Palladium is a transition metal of Group VIII of the periodic table. Salts of palladium may also be employed in preparing the Pd-lipoic acid complexes of the present invention. The palladium salts may be selected from, and are not limited to, for example, palladium acetate, palladium acetylacetonate, palladium ammonium chloride, palladium ammonium nitrate, palladium bromide, palladium chloride, palladium diamine nitrite, palladium diamylamine nitrite, palladium dibromide, palladium difluoride, palladium dioxide, palladium dipyridine nitrite, palladium ethylenediamine nitrite, palladium iodide, palladium monoxide, palladium nitrate, palladium oxalate, palladium oxide, palladium sulfate, palladium sulfide, palladium tetramine dichloride, palladous potassium bromide, palladous potassium chloride, palladous sodium bromide, and palladous sodium chloride. The preferred palladium salts are palladium chloride, palladium bromide, palladium iodide, palladium nitrate, palladium oxide and palladium sulfide. The most preferred palladium salt is palladium chloride.

While palladium or a salt thereof is required in the practice of the present invention, the complex may also further comprise an additional metal compound such as vanadate, molybdate, zinc or tin, or other cations such as potassium or sodium.

As discussed supra, at least two forms of the Pd-lipoic acid complex are useful in the practice of the present invention: [1] (palladium)$_m$(lipoic acid)$_n$ wherein m and n are both 1 (i.e., the 1:1 complex), and [2] (palladium)$_m$ (lipoic acid)$_n$ wherein m is 1 and n is 2 (i.e., the 1:2 complex). Other possible forms of the Pd-lipoic acid complex include (palladium)$_m$(lipoic acid)$_n$ wherein m is 2 and n is 1, and (palladium)$_m$(lipoic acid)$_n$ wherein m and n are both 2. With respect to the 1:1 and 1:2 complexes, studies have shown that the 1:2 complex has less biological activity than the 1:1 complex. While not wishing to be bound by any specific theory, the foregoing suggests that the second lipoic acid molecule competes with the palladium for interaction at the biological site. With respect to the various palladium-lipoic acid complexes possible, the equilibria of which complex is favored may be controlled by controlling the amount of lipoic acid introduced into the reaction.

Crystallographic studies, as illustrated in FIG. 1, show that the palladium-lipoic acid complex forms a trigonal prism. Trigonal prism symmetry is representative of an octa-coordinate molecule, as stated in Cotton et al., *Advanced Inorganic Chemistry*, Interscience, 29 (1972). The crystallographic studies as illustrated in FIG. 1 are thus consistent with the prior illustrations of the palladium-lipoic acid complexes set forth above which show octa-coordination.

Other Pd-lipoic acid complexes are also possible. For example, a dinuclear complex satisfies octa-coordination. In such a complex, two metal atoms share the center of symmetry of the complex with four coordinate covalent bonds between the lipoic acid molecules and the palladium ions. The four coordinate covalent bonds could be satisfied, for example, by having between two to four lipoic acid molecules bonded to the palladium ions. For example, a dinuclear 2(n=1) complex, wherein two palladium ions are present with each having one lipoic acid molecule bonded to it by two coordinate covalent bonds, could exist. Alternatively, the dinuclear complex could be a 2(n=2) complex, wherein two palladium ions are present with each having two lipoic acid molecules bonded to it. In this dinuclear complex, each lipoic acid is bonded by only one coordinate covalent bond to each palladium ion. In the present invention, the dinuclear 2(n=1) complex is preferred.

Oxidized and reduced forms of the palladium-lipoic acid complex are also contemplated. Whether the oxidized or reduced form is favored will depend upon the pH of the particular solution containing the Pd-lipoic acid complex.

The palladium-lipoic acid complex of the present invention may be produced by dissolving lipoic acid in a basic solution and adding that to an acidic solution containing palladium or a salt thereof. The resulting solution is heated to a boil, e.g., to about 100° C., to produce the Pd-lipoic acid complex. More specifically, the palladium-lipoic acid complex of the present invention may be synthesized by the following procedure:

(a) adding palladium or a salt thereof to an acidic solution;

(b) heating the palladium-acidic solution to at least about 100° C.;

(c) filtering the palladium-acidic solution from step (b);

(d) dissolving lipoic acid in a basic solution;

(e) adding the dissolved lipoic acid solution from step (d) to the palladium solution from step (c); and (f) heating the lipoic acid-palladium solution to at least about 100° C., for an amount of time sufficient to obtain a palladium-lipoic acid complex.

The palladium or salt thereof is added to the acidic solution in a mole ratio of between about 1 and about 2 moles palladium to moles acid. Any method for mixing the palladium and acidic solution may be used, for example, stirring or agitation. The palladium-acidic solution may then be heated to a gentle boil, e.g., at least about 100° C., preferably between about 100° and about 200° C., and most preferably at about 100° C.

The acidic solution to which the palladium is added is selected from acids well known in the art. Such acids include perchloric acid, sulfuric acid, hydroiodic acid, hydrobromic acid, hydrochloric acid, nitric acid, phosphoric acid, nitrous acid, acetic acid, carbonic acid, and hydrogen sulfide. Preferably, the acidic solution is hydrochloric acid.

The palladium-acidic solution may be filtered by any method generally known in the art. Such methods include, for example, gravity filtration, suction filtration, centrifugation or the like.

In a separate container, lipoic acid is added to the basic solution in a mole ratio of between about 1 and about 7 moles lipoic acid to mole base. Any method for mixing the lipoic acid-basic solution may be used, for example, stirring or agitation. Any of the above methods of filtration may then be used to eliminate any undissolved residue. The solution is preferably filtered to complete clarity.

The basic solution in which the lipoic acid is dissolved can be selected from bases known in the art, for example, sodium hydroxide, ethanolamine, potassium hydroxide, sodium acetate, dimethyl amine, diethyl ether, ethanol and the like. Preferably, the basic solution is sodium hydroxide.

Next, the dissolved lipoic acid solution is added to the palladium solution. The palladium-lipoic acid solution is heated to a gentle boil, e.g., to at least about 100° C., preferably to between about 100° and about 200° C., and most preferably to about 100° C. The solution is generally allowed to boil for about 10 minutes. When the palladium and lipoic acid react, a clear dark red solution is produced. The pH of the palladium-lipoic acid solution can be adjusted to at least about 6, preferably to a pH between about 6 and about 7, and more preferably to a pH of about 6.8.

In the practice of the present invention, water may be added to the palladium-lipoic acid solution in an amount sufficient to obtain a concentration of the palladium-lipoic acid complex of at least about 0.01M, preferably between about 0.01M and about 0.08M, and most preferably in an amount sufficient to obtain a concentration of about 0.04M.

This resulting Pd-lipoic acid complex has been designated by the present inventor as Polynucleotide Reductase Core, referred to herein as "Poly-RC." Other ingredients may be added to Poly-RC to enhance its chemical and biological activity. For administration to humans, the pH of the complex is preferably adjusted to about 6.8 by the addition of an acid, if necessary, and the concentration is preferably adjusted to about 0.04M by the addition of a sufficient amount of water. This solution of the complex is stable and may be easily stored at room temperature.

One preferred embodiment of the present invention comprises a Pd-lipoic acid complex to which thiamine or a salt thereof has been added. The thiamine salt will be bound to the palladium metal ion at the $N_1$ nitrogen of the pyrimidine ring of thiamine. Hadjiliadis et al., "Interaction of Thiamine and its Phosphate Esters with Pt(I) and Pd(II)," *Inorganica Chimica Acta* 25L21–31 (1977). Any thiamine salt is useful in the practice of the present invention. Preferably, the thiamine salt is selected-from-thiamine hydrochloride, thiamine nitrate, thiamine phosphate, and thiamine pyrophosphate. Most preferably, the thiamine salt is thiamine hydrochloride. The thiamine or a salt thereof may be added to the Pd-lipoic acid solution after the Pd-lipoic acid solution is cooled to at least about 55° C., preferably to between about 20° and about 50° C., and most preferably to about 42° C. The solution may be cooled by any method known in the art.

While the thiamine or salt thereof is being added to the solution containing the palladium-lipoic acid complex, mixing of the thiamine with the Pd-lipoic acid solution can be facilitated, for example, by stirring or agitation of the solution. The resulting solution may then be filtered, preferably sterile-filtered, by methods known in the art. The resulting novel composition has been designated by the present inventor as Polynucleotide Reductase-2, referred to herein as "Poly-R2". The pH of Poly-R2 is adjusted to at least about 6, preferably to a pH between about 6 and about 7, and more preferably to a pH of about 6.5.

Sufficient water should be added to the palladium-lipoic acid solution to obtain a concentration of the palladium-lipoic acid-thiamine complex in the Poly-R2 of at least about 0.01M, preferably between about 0.01M and about 0.08M, and most preferably in an amount sufficient to obtain a concentration of about 0.04M in the resulting composition. Poly-R2 is stable and may be easily stored at room temperature.

A further preferred embodiment comprises a thiamine salt of the Pd-lipoic acid complex to which a synthetic, i.e., activated, cofactor of vitamin $B_{12}$ (cyanocobalamin) is added. The vitamin $B_{12}$ cofactor of the complex is cyanocobalamin which has been reacted with acetylcysteine. This thiamine salt of the Pd-lipoic acid complex having an activated cofactor of vitamin $B_{12}$ has been shown to exhibit even more enhanced biological activity than the Poly-RC and Poly R2. This Pd-lipoic acid derivative is referred to herein as $B_{12}$AC-Poly-R2.

The activated $B_{12}$ is prepared by mixing equal amounts of cyanocobalamin and acetylcysteine in a sufficient amount of water to dissolve both of the substances. The pH of the activated $B_{12}$ solution is preferably adjusted to at least about 6, preferably to a pH between about 6 and about 7, and more preferably to a pH of about 6.5. For example, NaOH may be added to the solution to adjust the pH to about 6.5 in a particularly preferred embodiment. The solution is then boiled for about 10 minutes.

The activated $B_{12}$ is added to the Poly-R2 solution prior to the addition of water to adjust the concentration of the Poly-R2. The amount of activated $B_{12}$ added is generally in the range of about 0.1 to about 5 grams in 20 liters of Poly-R2. Sufficient water should then be added to the solution to obtain a concentration of the activated $B_{12}$-palladium-lipoic acid-thiamine complex in the $B_{12}$AC-Poly-R2 of at least about 0.01M, preferably between about 0.01M and about 0.08M, and most preferably in an amount sufficient to obtain a concentration of about 0.04M in the resulting composition. $B_{12}$AC-Poly-R2 is stable and may be easily stored at room temperature.

The palladium-lipoic acid complexes, e.g., Poly-RC, Poly-R2 and $B_{12}$AC-Poly-R2, may be identified using UV-visible spectroscopy, and preferably by cyclic voltammetry, as discussed further in the Examples. The structures of these complexes, as shown in the Examples, were also studied by Fourier transform-infrared spectroscopy (FTIR). Cyclic voltammetry was performed to demonstrate the charge interactions of the palladium-lipoic acid complexes with DNA or RNA. Such studies were performed using Poly-RC, Poly-R2 and $B_{12}$AC-Poly-R2 with DNA and Poly-R2 with RNA. These studies illustrated that the palladium-lipoic acid complexes of the present invention shunt electron energy from the complexes to nucleic acids of DNA or RNA and are polynucleotide reductases. The results of these studies are further discussed in the Examples.

The present inventor has also found that these novel polynucleotide reductases induce new varieties of cell forms in amoeba, yeast and mold. For example, these reductases produce giant Baker's yeast cells. They also induce micronucleated nuclei in Baker's yeast, amoeba, and tumors. In addition, the polynucleotide reductases of the present invention cause formation of multiple spore bearing sori on the stalks of the mold *Dictyostelium discoideum*.

These novel polynucleotide reductases have also been found to induce dense granular chromatin in the nuclei of amoeba, yeast and mold. The dense form of chromatin produced in cells is generally referred to as heterochromatin. Manuelidis, "A View of Interphase Chromosomes" *Science* 250:1533–1540 (Dec. 14, 1990); and Yunis et al., "Heterochromatin, Satellite DNA, and Cell Function" *Science* 174:1200–1208 (Dec. 17, 1971). During cell replication, for the chromosomes to condense in metaphase, metabolic energy is required. As the condensation of chromatin is known to be energy dependent (Manuelidis et al.), these studies would further support the inventor's belief that the effect of Poly-RC, Poly-R and $B_{12}$AC-Poly-R2 on DNA and RNA is an electron transfer reaction.

While not wishing to be bound by any theory, the present inventor believes that the novel polynucleotide reductases induce energy dependent conformational changes in DNA and RNA. These conformational changes in DNA and RNA result from the nucleic acids being in a more reduced state as a result of electron transfer upon interaction with the polynucleotide reductases of the present invention.

The present invention also provides a pharmaceutical composition of matter comprising a pharmaceutically effective amount of the complexes previously described, e.g., the palladium or a salt thereof and lipoic acid or a derivative thereof complex, the palladium-lipoic acid complex which further comprises thiamine or a salt thereof, or the thiamine-palladium-lipoic acid complex which further comprises a synthetic cofactor of vitamin $B_{12}$ (cyanocobalamin), and a pharmaceutically acceptable carrier therefor. Preferably, the pharmaceutical composition comprises a (palladium)$_m$ (lipoic acid)$_n$ complex, wherein m and n are each independently 1 or 2, and more preferably, wherein m is 1 and n is 1. In a further preferred embodiment, the pharmaceutical composition comprises the palladium-lipoic acid complex in a solution in an amount sufficient to obtain a concentration of about 0.04M. For the pharmaceutical composition comprising the thiamine-palladium-lipoic acid complex which further comprises a synthetic cofactor of vitamin $B_{12}$ (cyanocobalamin), 1000 μg of vitamin $B_{12}$ (cyanocobalamin) will preferably be present in a 10 ml dose of the thiamine salt of the palladium-lipoic acid complex.

The pharmaceutically acceptable carriers of the present invention depend on the dosage form selected and are carriers which are well known in the art. Different routes of administration necessarily require different pharmaceutically acceptable carriers. An identification of such carriers may be found in any standard pharmacy text, for example, *Remington's Pharmaceutical Sciences*, 17th edition, ed. Alfonso R. Gennaro, Mack Publishing Company, Easton, Pa. (1985). More specifically, examples of pharmaceutically acceptable carriers include pharmaceutical diluents, excipients or carriers suitably selected for the intended route of administration which is consistent with conventional pharmaceutical practice. For instance, for oral administration in the form of tablets or capsules, the active drug components may be combined with any oral non-toxic pharmaceutically acceptable inert carrier such as starch, cellulose, magnesium stearate, dicalcium phosphate, calcium sulfate, mannitol, and the like. Moreover, when desired or necessary, suitable binders, lubricants, disintegrating agents and coloring agents can also be incorporated in the mixture. Suitable binders, for example, include starch, gelatin, natural and synthetic gums such as acacia, sodium alginate, carboxymethylcellulose, polyethylene glycol and waxes. Among the lubricants, there may be mentioned for use in these dosage forms, boric acid, sodium benzoate, sodium acetate, sodium chloride, etc. Disintegrators include, without limitation, starch, methylcellulose, agar, bentonite, guar gum, etc. Flavoring agents and preservatives can also be included where appropriate. In the case of tablets, they can be further coated with the usual coating materials to make, for example, sugar-coated tablets, gelatin film-coated tablets, tablets coated with enteric coatings, tablets coated with films or double-layered and multi-layer tablets.

For parenteral administration, for example, the formulations must be sterile and pyrogen-free, and are prepared in accordance with accepted pharmaceutical procedures, for example as described in *Remington's Pharmaceutical Sciences* at pp. 1518–1522. The aqueous sterile injection solutions may further contain anti-oxidants, buffers, bacteriostats, isotonicity adjusters and like additions acceptable for parenteral formulations. Various unit dose and multidose containers, e.g., sealed ampules and vials, may be used, as is well-known in the art. The essential ingredients of the sterile parenteral formulation, e.g., the water and the selected palladium-lipoic acid complex, may be presented in a variety of ways, just so long as the solution ultimately administered to the patient contains the appropriate amounts of the essential ingredients. Thus, for example, the palladium-lipoic acid complex/water formulation may be presented in a unit dose or multidose container, ready for injection. As another example, a concentrated solution of palladium-lipoic acid complex/water may be presented in a separate container from a diluting liquid (water or palladium-lipoic acid complex/water) designed so that the contents can be combined to give a formulation containing appropriate amounts for injection. As another alternative, the palladium-lipoic acid complex may be provided in a freeze-dried condition in one container, while a separate container contains diluting liquid (water or palladium-lipoic acid complex/water, depending on the amount of palladium-lipoic acid complex in the other container), again designed so that the contents can be combined to give a formulation containing the appropriate amounts of the water and selected palladium-lipoic acid complex. In any event, the contents of each container will be sterile. Suitable carriers for parenteral administration include, for example, water, ethyl alcohol, propylene glycol, ethoxylated isostearyl alcohol, polyoxylated isostearyl alcohol, polyoxyethylene sorbitol and sorbitate esters. In these instances, adequate amounts of sodium chloride, glucose or glycerin can be added to make the preparations isotonic.

As previously stated, the synthetic polynucleotide reductases have been found to be useful as therapeutic agents for cancer and the treatment of psoriasis. Data reporting therapeutic effects are best presented by independent institutional protocols. Compassionate Investigational New Drug studies in humans involving administration of the novel polynucleotide reductases were begun in November of 1992 and are presently ongoing. As of Feb. 3, 1993, eighty patients with tumors have been treated with Poly-R2. As of the filing date of the present application, approximately 800 patients have been treated with $B_{12}AC$-Poly-R2. These terminally ill patients have experienced a reduction in tumor size by objective criteria and subjective relief of symptoms caused by various cancers.

For example, Poly-R2 has also been administered to patients having metastatic lesions to the liver. In these patients, the serum albumen levels return to normal after treatment with Poly-R2. Moreover, the enlargements of the liver become no longer palpable.

With respect to the range of tumor types responding to Poly-RC, Poly-R2, and $B_{12}AC$-Poly-R2, oncologists are using these polynucleotide reductases "across the board," e.g., for treatment of carcinomas and adenocarcinomas of the lung, breast, colon, esophagus, or pancreas; malignant melanomas; liver metastases; or AIDS-related lymphomas or sarcomas. Specific lesions undergoing liquefaction at this time include adenocarcinomas of the breast and bowel, and pancreatic and lung carcinomas. Malignant melanomas and liver metastases are also presently being treated with Poly-RC, PolyR2, and $B_{12}AC$-Poly-R2. Such carcinomas, adenocarcinomas, melanomas and metastases are shrinking and developing non-hemorrhagic central liquefaction after treatment with Poly-RC, Poly-R2, and $B_{12}AC$-Poly-R2. $B_{12}AC$-Poly-R2 is particularly preferred for the above methods of treatment. Oncologists have also stated that the pattern of their practice has changed as there are now fewer weekend emergencies involving the oncological patients being treated with these polynucleotide reductases.

$B_{12}AC$-Poly-R has also been found useful for the treatment of psoriasis. For the treatment of psoriasis, the $B_{12}AC$-Poly-R2 is preferably topically administered to the afflicted area of the patient, however, other forms of administration including oral and parenteral may be useful in the practice of the present invention. Examples of types of psoriasis which may be treated include psoriasis vulgaris. Psoriasis vulgaris has been treated topically with a 0.04M $B_{12}AC$-Poly-R2 solution. At present, 10 patients have received $B_{12}AC$-Poly-R for the treatment of psoriasis. Patients with severe psoriasis having thick, large plaques involving greater than 40% of their body surface were chosen for treatment. After one week of treatment involving application of $B_{12}AC$-Poly-R one to two times daily, significant objective improvement of psoriatic lesions were observed. Scaling, thickness, roughness and inflammation of psoratic plaques were reduced by at least 50%. In some treated areas, the psoriatic plaques have been sufficiently reduced for normal skin markings, e.g., stretch marks and skin creases, to again be evident in the lesional areas. FIGS. 10A, 10B, 10C and 10D illustrate the effect of $B_{12}AC$-Poly-R2 when used to treat severe psoriasis. While no treated plaques have been completely resolved and cleared, the positive therapeutic effects observed after a relatively short period of topical treatment have been quite significant. Further prolonged studies of the effects of Poly-R on psoriasis are still ongoing as of the filing date of this patent application.

The dosage of the compositions of the present invention is selected, for example, according to the usage, purpose and conditions of symptoms. Furthermore, the dose administered will be selected, for example, according to the particular composition employed and the size and condition of the patient as well as the route of administration employed, but in any event will be a quantity sufficient to cause a reduction in tumor size or a reduction of maculopapules associated with psoriasis.

For tumors, Poly-RC, Poly-p or $B_{12}AC$-Poly-R2 is administered to a patient in an amount effective for tumor reduction to a patient in need of such treatment. A parenteral route of administration is preferred including, for example, intravenous, intramuscular, subcutaneous, intradermal, topical, intrathecal and intraarterial methods. More preferably, the pharmaceutical composition of the present invention is parenterally administered to a patient at a dosage of between about 5 and about 30 ml daily of a 0.04M solution of the pharmaceutical composition for at least about 5 days. At present, the prevailing dosage pattern in adult humans has been 40.0 ml of 0.04M Poly-RC, Poly-R2 or $B_{12}$AC-Poly-R2 administered daily for the first three days of treatment, followed by 20.0 ml daily for an additional 14 days of treatment. Alternatively, a pharmaceutical composition comprising $B_{12}$AC-Poly-R2 may be administered to a patient at a dosage of about 40 ml for about 10 days. However, the precise route of administration, dosage and frequency of administration is individualized for each patient and can vary over a wide range depending on the particular disease state being treated, the condition of the patient and the like.

For the treatment of psoriasis, the pharmaceutical compositions of the present invention are administered in an amount effective for reduction of maculopapules associated with psoriasis to a patient in need of such treatment. Parenteral routes of administration, in particular topical, are preferred. Preferably, the thiamine salt of the palladium-lipoic acid complex, and more preferably the thiamine salt of the palladium-lipoic acid complex which further comprises a synthetic cofactor of vitamin $B_{12}$, is topically administered to a patient at a dosage of between about 5 and about 80 ml daily of a 0.04M solution for at least about 5 days. For psoriasis, the prevailing dosage has been between about 5 and about 10 ml of $B_{12}$AC-Poly-R2 topically administered one to two times daily on the area to be treated for about one week. A 10 ml dose of $B_{12}$AC-Poly-R2, for example, will comprise approximately 210.0 mg of the thiamine salt of a palladium-lipoic acid complex composition and 1000 µg of the activated $B_{12}$ compound. Subsequent dosages are then determined by observation of the response to the composition and further evaluation of the patient. Once again, treatment is individualized. The patient may be reevaluated at any time in order to determine whether treatment should be continued and at what dosage.

Higher dosages of the palladium-lipoic acid complexes, or polynucleotide reductases, are generally administered intravenously, while lower dosages may be given by any injectable route. There has been no observable toxicity at the dosages presently contemplated, including 100.0 ml of 0.04M solution of $B_{12}$AC-Poly-R2 administered intravenously. The intraperitoneal LD 50 in 20.0 g hybrid Swiss mice is 0.80 ml of this solution, which extrapolates to approximately 800.0 ml in humans. The dosage range of the novel palladium-lipoic acid complexes, or polynucleotide reductases, of the present invention is about 500 to about 2000 mg daily. Treatment including dosages and routes of administration as indicated above is individualized and is determined by a clinician and depends on a variety of factors including the specific disease state treated, the condition of the patient, and the like.

The present invention also includes pharmaceutical compositions comprising the novel palladium-lipoic acid complexes as previously described supra. In general, the pharmaceutical compositions of the present invention may be administered by any parenteral route, with intravenous, intramuscular, subcutaneous, intradermal, topical, intrathecal and intraarterial methods being preferred for the treatment of tumors. At present, for example, up to 100.0 ml of $B_{12}$AC-Poly-R2 has been injected intravenously without any adverse response by the treated patient. Oral forms of palladium-lipoic acid complexes may also be suitable for the practice of the present invention. For the treatment of psoriasis, topical administration of the pharmaceutical compositions of the present invention to the affected area is preferred.

In order to further illustrate the present invention, the following specific examples are given, it being understood that the same are intended as illustrative and in nowise limitative.

EXAMPLES

Example 1

Preparation of Polynucleotide Reductase (Poly-RC)

The following substances were obtained for laboratory use: de-ionized distilled water, palladium dichloride (Sigma) and lipoic acid (Fluka).

A solution of 80.0 ml of 1.0N HCl was placed in a 2000 ml multi-necked spherical glass reactor vessel in a hemispheric heater. 7.10 g of $PdCl_2$ was then added to the HCl solution. The reactor vessel was stirred with a lightning type mixer. The shaft and rotor of all reactors were plastic-coated so that no metal was exposed to the solutions. The solution was brought to a gentle boil for ten minutes. The boiling temperature was close to that of water, e.g., about 100° C. The color of the solution upon boiling was a clear dark amber. Once a clear, dark amber solution was achieved, this solution was removed from the reactor, filtered to clarity, and replaced in the rinsed 2000 ml reactor.

In a separate beaker 8.26 g of lipoic acid was stirred and dissolved in 285 ml of 1.0N NaOH. If any undissolved residue remained, the solution was filtered to complete clarity.

The dissolved lipoic acid was next added to the palladium solution with stirring and continued heating until the solution was brought to a gentle boil. The boiling temperature is close to that of water, e.g., 100° C. After ten minutes of boiling, a clear dark red solution was produced. This solution contained the essential core complex: Pd-lipoic acid, i.e., Poly-RC.

The pH of the Poly-RC was adjusted to 6.8 by the addition of 1.0N HCl. Water was added to adjust the volume to 1000 ml. The concentration of the resulting palladium-lipoic acid complex was 0.04M.

Example 2

Preparation of Polynucleotide Reductase-2 (Poly-R)

In order to prepare Polynucleotide Reductase-2 (Poly-R2), 9.0 g of thiamine-HCl (Fluka), was dissolved in 200 ml water.

When the red Pd-lipoic acid solution containing the essential Pd-lipoic acid core complex produced in Example 1 had cooled to 42° C., the thiamine-HCl solution was added with vigorous stirring. The pH was 6.5. The total volume of the thiamine salt of a palladium-lipoic acid complex solution was adjusted to 1000 ml by the addition of water. The solution was next sterile-filtered through a 0.2 micron pore membrane flask. Water was added to adjust the volume to 1000 ml, resulting in a 0.04M solution of Poly-R2.

Example 3

Preparation of $B_{12}$AC-Poly-R2

In order to prepare $B_{12}$AC-Poly-R2, 100 mg of cyanocobalamin (Sigma), was mixed with 100 mg of acetylcysteine (Fluka), and dissolved in 20.0 ml of water. The pH was adjusted to 6.5 by the addition of NaOH, and the resulting solution was then boiled for 10 minutes. The solution was cooled and then mixed with the Poly-R2 which was obtained prior to adjusting the volume to 1000 ml in Example 2. Water was next added to adjust the volume to 1000 ml, resulting in a 0.04M solution of $B_{12}$AC-Poly-R2 based on the Poly-2 concentration. The cyanocobalamin concentration was 0.1 mg/ml.

Example 4

Figure 2A:
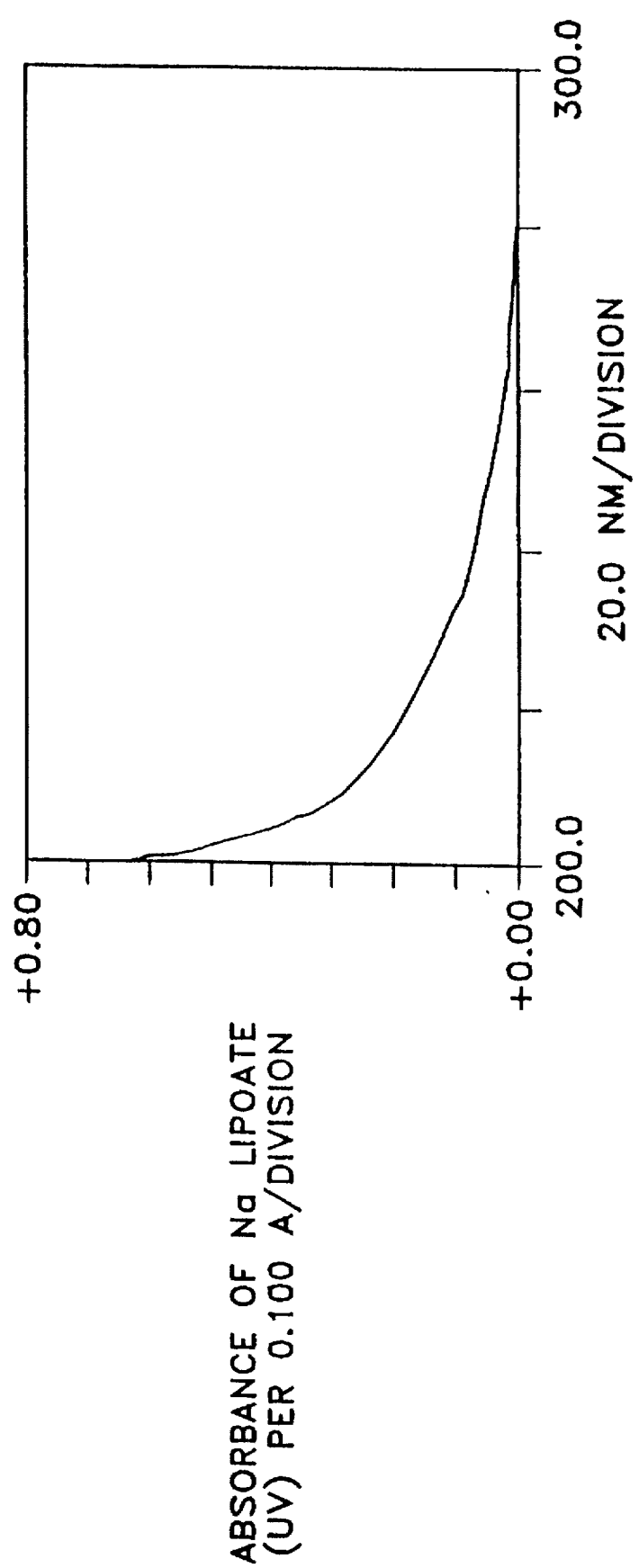
FIG. 2A shows an ultraviolet spectra of uncomplexed sodium lipoate, aqueous $10^{-4}$ molar (experiment conducted Jun. 11, 1993). There is no UV peak.

Identification of Poly-C, Poly-R and $B_{12}$AC-Poly-R2 Using UV-visible spectroscopy An ultraviolet spectra of uncomplexed sodium lipoate in solution ($10^{-4}\mu$) was first conducted using a Shimadzu UV-160U recording Spectrophotometer. This spectra is shown in FIG. 2A. This figure shows that UV absorbance peaks do not result from a solution of uncomplexed sodium lipoate. In addition, the almost clear solution had no absorbance peaks in the visible region.

Figure 2B:
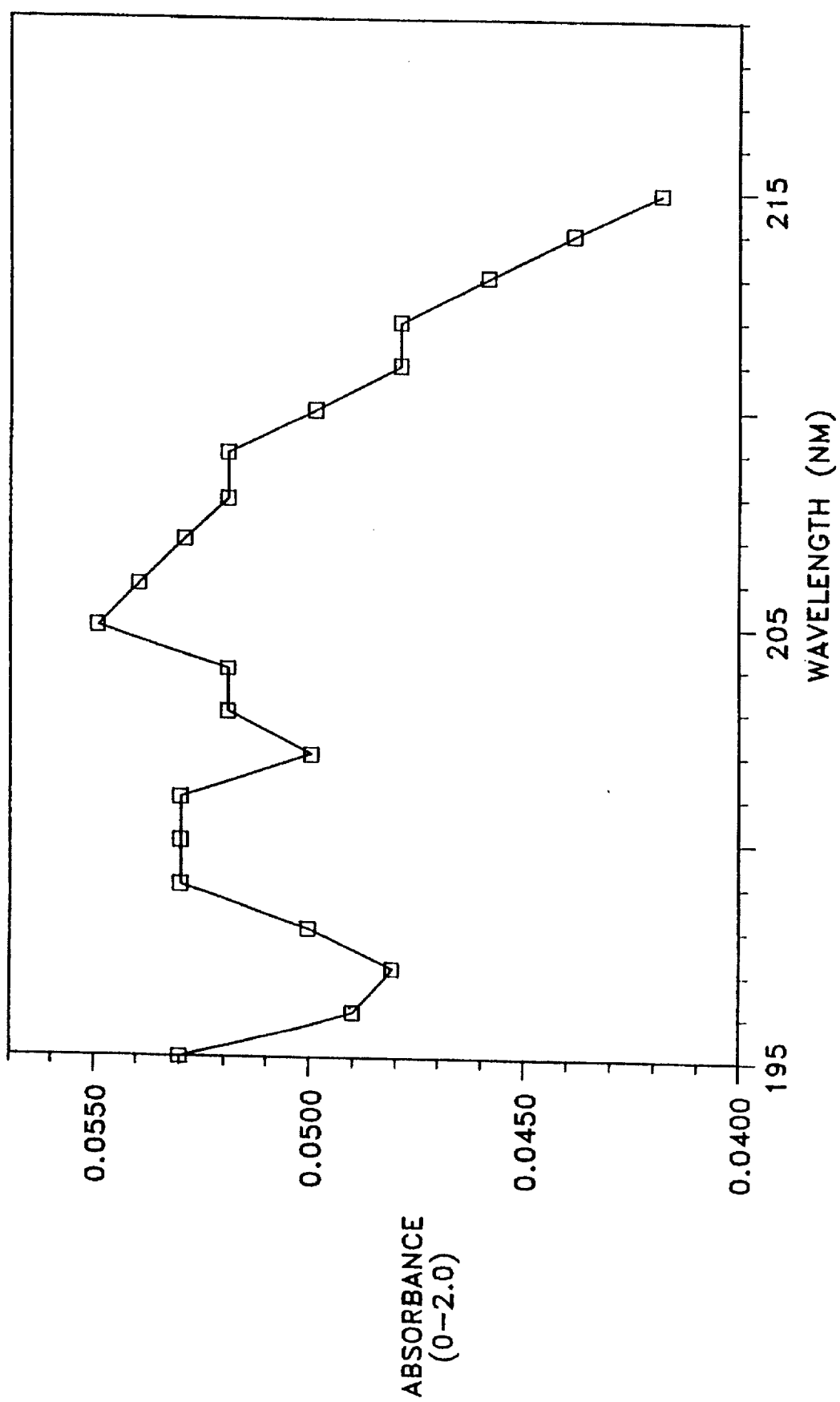
FIGS. 2B and 2C show ultraviolet spectra of Pd-Lipoic Acid Complex (Poly-RC) with a concentration of $2 \times 10^{-6}$M in FIG. 2B and $10^{-6}$M in FIG. 2C.
Figure 2C:
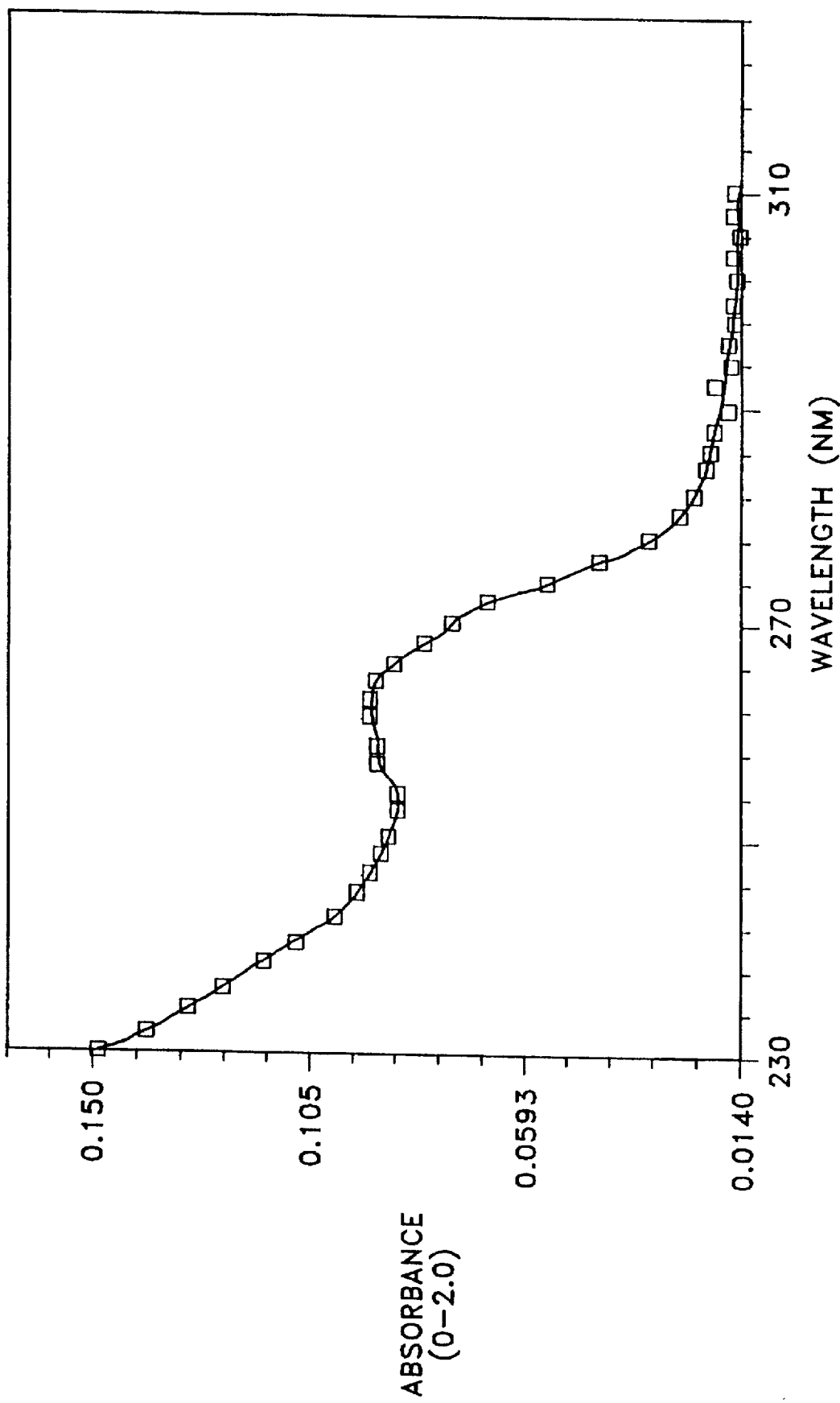

The ultraviolet spectra of Poly-RC was observed on an Hitachi model 440 Spectrometer with a 2 nm bandpass and is shown in FIGS. 2B and 2C. For the spectra of FIG. 2B, a $2\times10^{-6}\mu$ solution was used, while for FIG. 2C, a $10^{-6}\mu$ solution was used. The resulting peaks may be interpreted using any spectrophotometry text, for example Shugar et al., *The Chemist's Ready Reference Handbook*, McGraw-Hill, p. 6.19 (1990).

Poly-RC had absorbance peaks at 200, 205, and 261 nm and minima at 197, 202, and 253 nm.

Figure 2D:
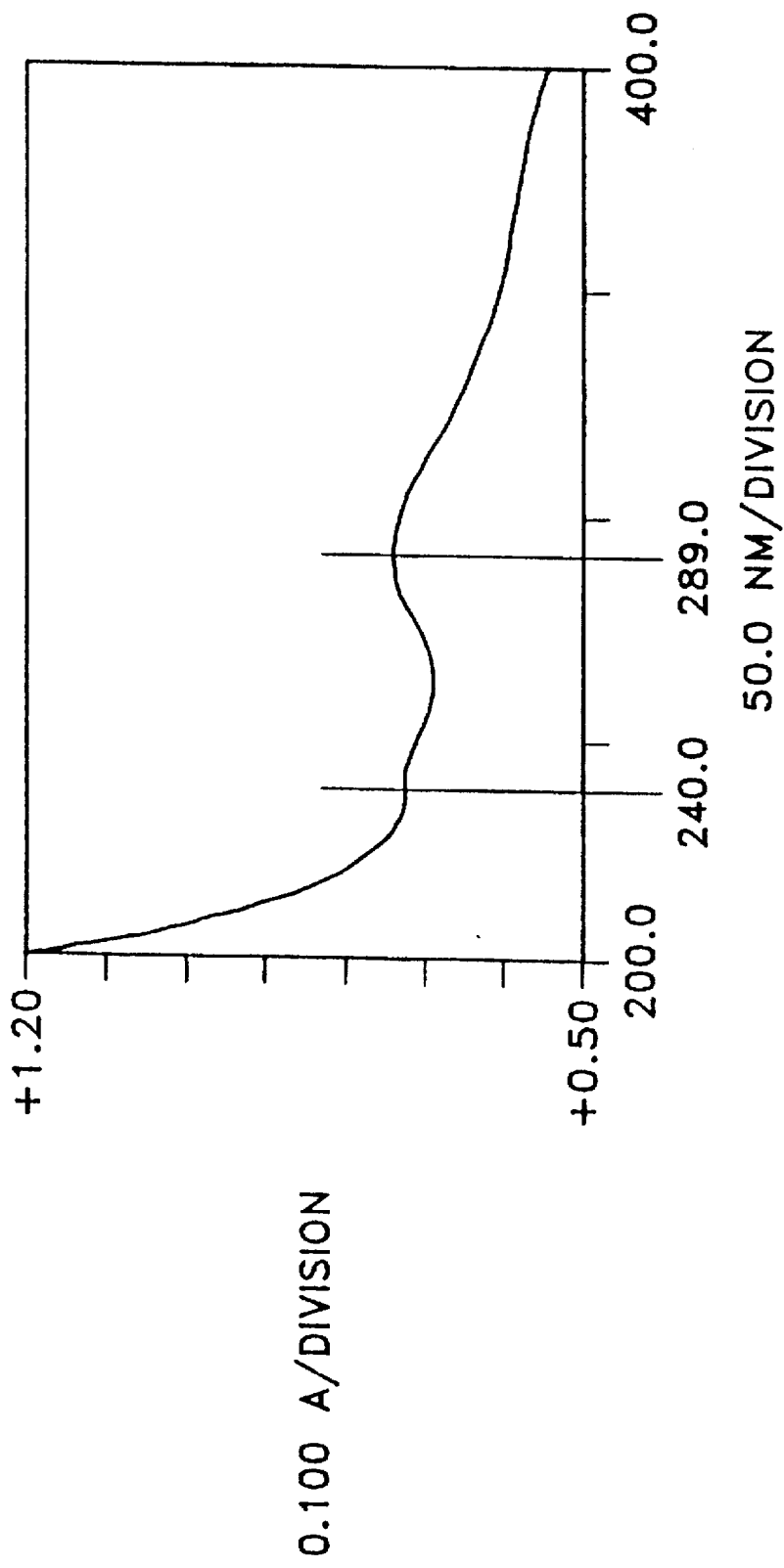
FIGS. 2D and 2F show ultraviolet absorbance spectra of oxidized Poly RC after ninety days of air oxidation of the solution (experiment conducted Jun. 11, 1993).
Figure 2E:
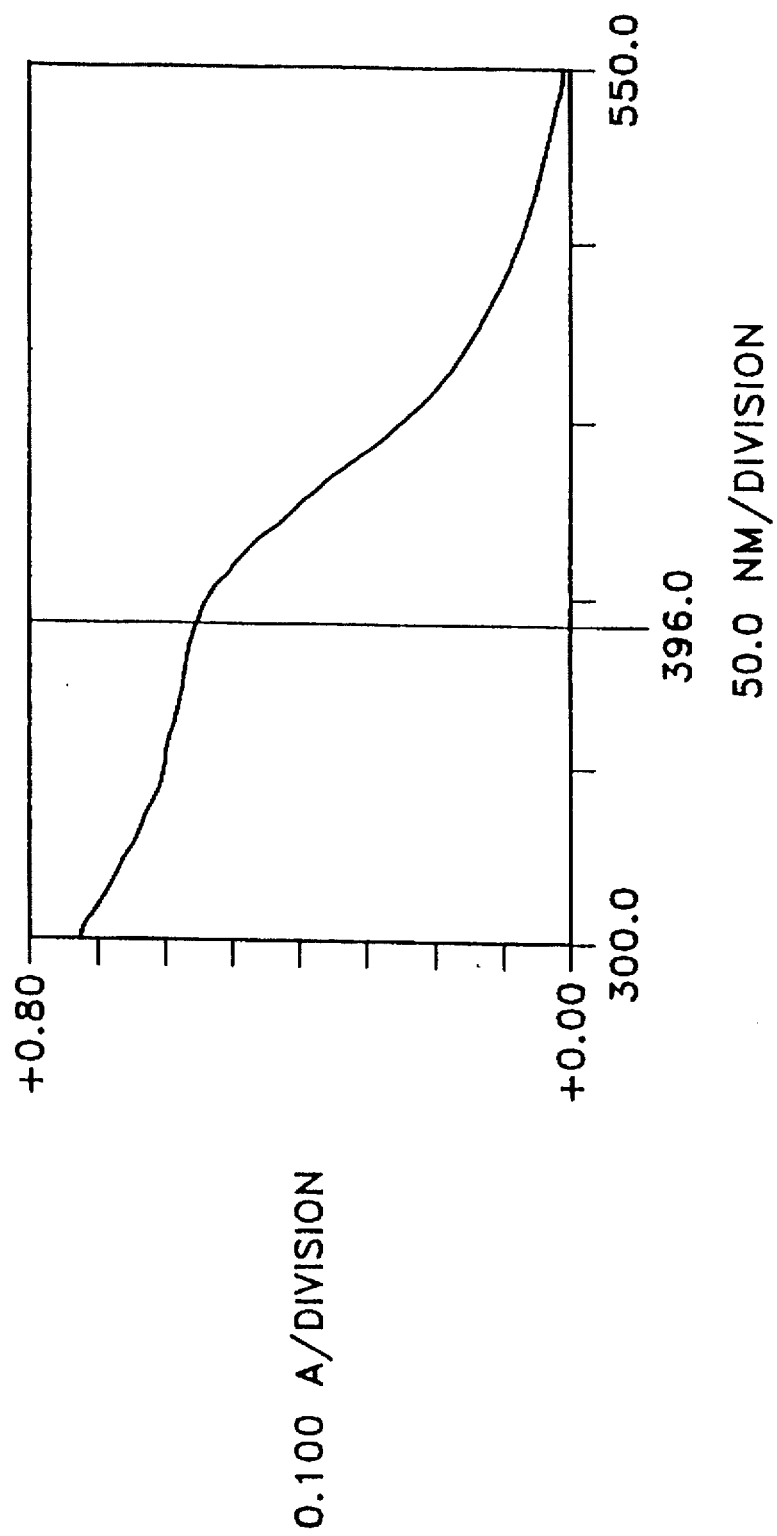

After ninety days of air oxidation of the Poly-RC solution, an ultraviolet spectra was again obtained on the Shimadzu UV spectrophotometer. These spectra are shown in FIGS. 2D and 2E. In both instances, a $1.2\times10^{-4}\mu$ solution was employed. As can be seen in FIG. 2D, Poly RC is in the oxidative state which is evidenced by the UV absorbance peaks at 240 nm and 289 nm. FIG. 2E illustrates the visible range of the Poly RC, in which range an inflection is estimated as occurring at 396 nm. These spectra showing a shift from the fresh Poly RC solution are consistent with the view that Poly RC is a redox complex.

Figure 2F:
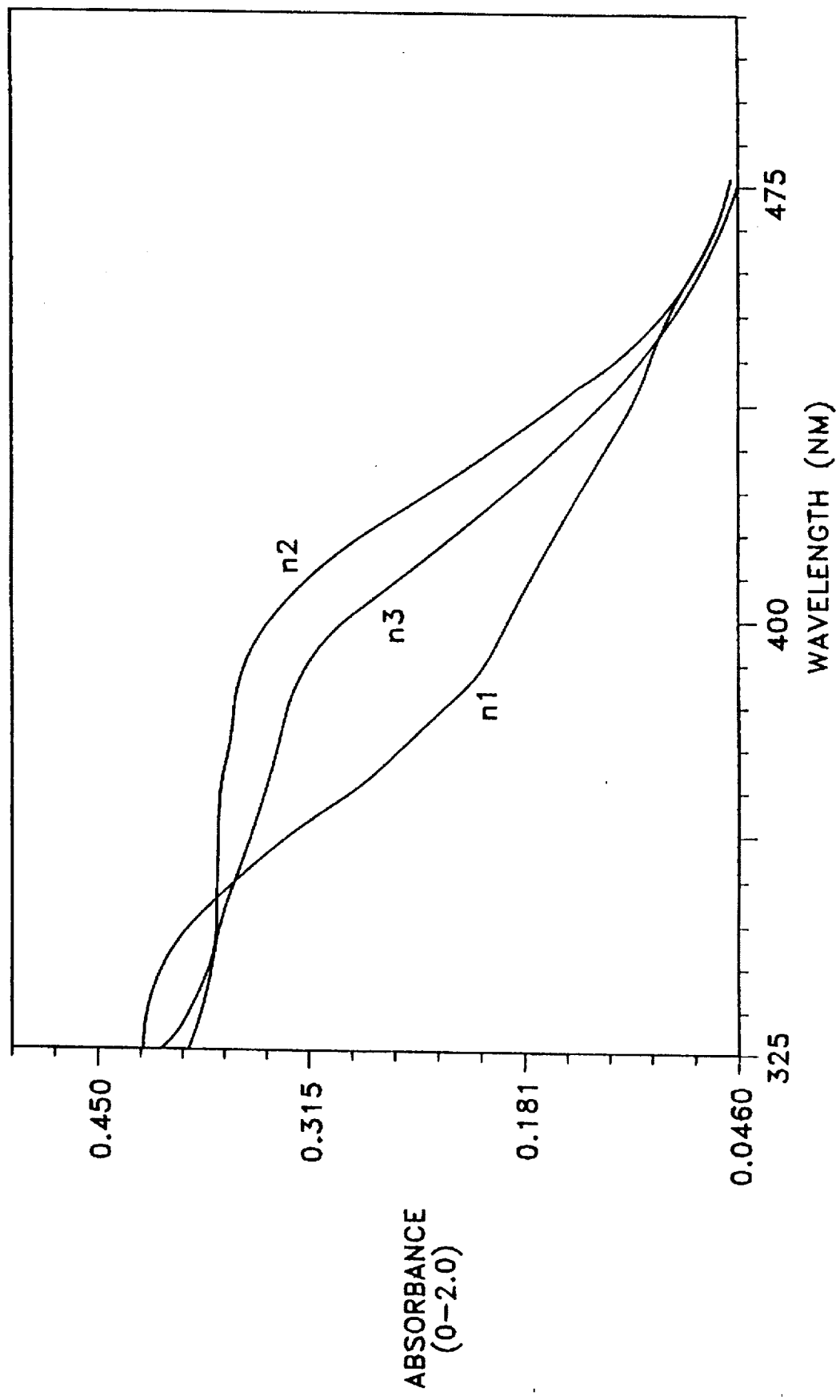

Stoichiometric studies of various Poly-RC solutions were performed in the visible range. FIG. 2F shows the visible absorbance spectra of the palladium-lipoic acid complex made at various ratios of ligand to metal. This preliminary work suggested that there are at least two forms of Pd-lipoic acid complex (as previously illustrated in the specification): (1) A 1:1 ratio of palladium to lipoic acid (n1), and (2) A 1:2 ratio of palladium to lipoic acid (n2). The 1:2 form showed a stronger red-shifted absorbance. Interestingly, however, this 1:2 form appeared to have less biological activity. This suggested that the second lipoic acid competes with the biologic site for interaction with the palladium. The 1:3 mixture of Pd-lipoic acid (n3) showed an unexpected intermediate absorbance curve. While this requires further study, it is presently viewed to be a mixture of the palladium-lipoic acid complexes having 1:1 and 1:2 ratios of Pd to lipoic acid.

Figure 2G:
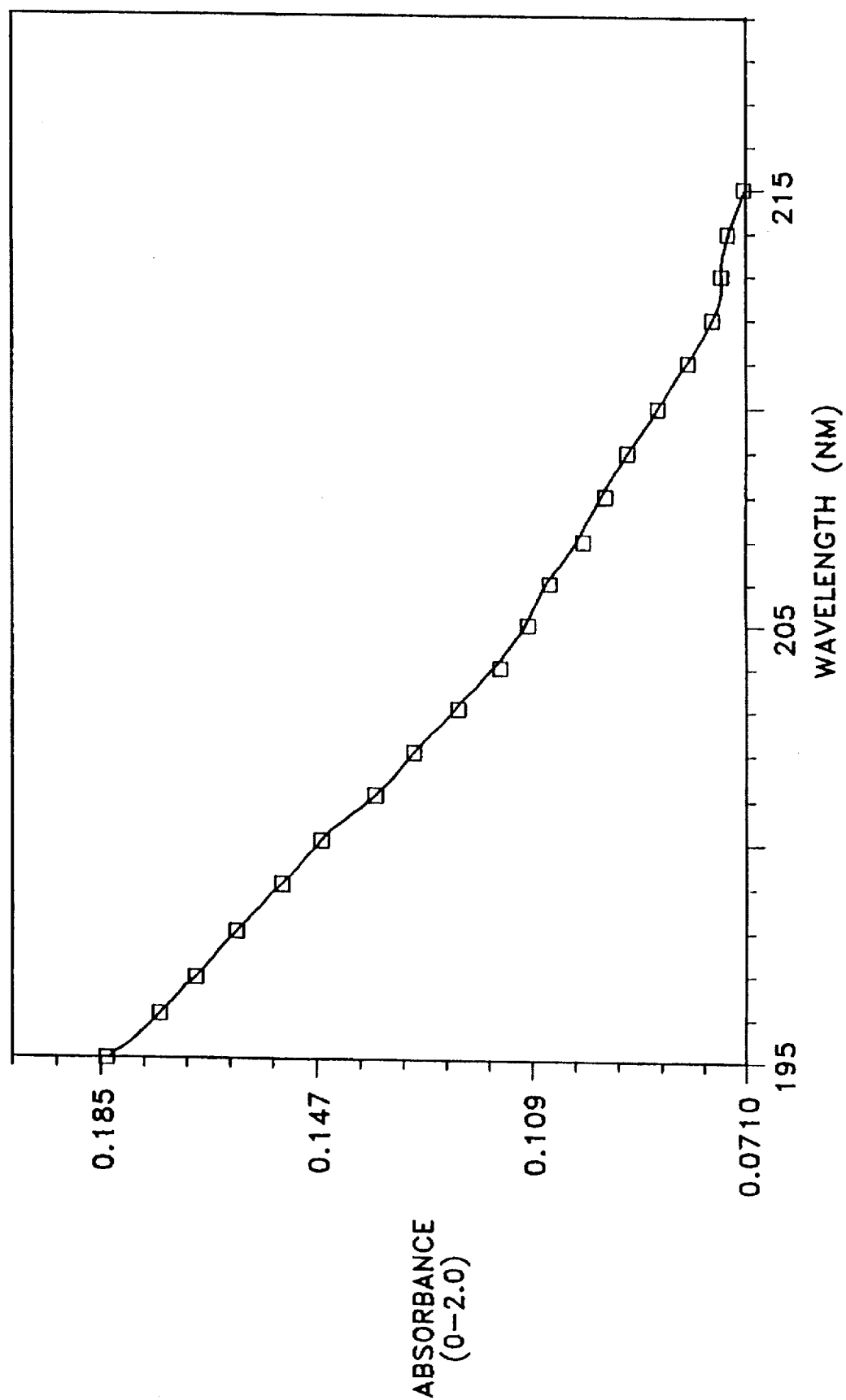
FIG. 2G illustrates an ultraviolet spectra of Poly-R2 (concentration $2 \times 10^{-6}$M) at frequencies between 195 and 215 nm.

Poly-R2 differs from Poly-RC by the addition of thiamine-HCl to the Pd-lipoic acid solution. It is notable that the palladium chloride solution forms a bright red solution when it is mixed with the thiamine-HCl solution with a Pd:thiamine ratio of 1:2, and the pH is adjusted to 6.5 with NaOH. FIG. 2G shows the absorbance spectra of a $3\times10^{-6}\mu$ solution of Poly-R2. The spectral character indicates that the thiamine interacts with palladium and can form interactive salts such as the thiamine salt of a palladium-lipoic acid complex.

Figure 2H:
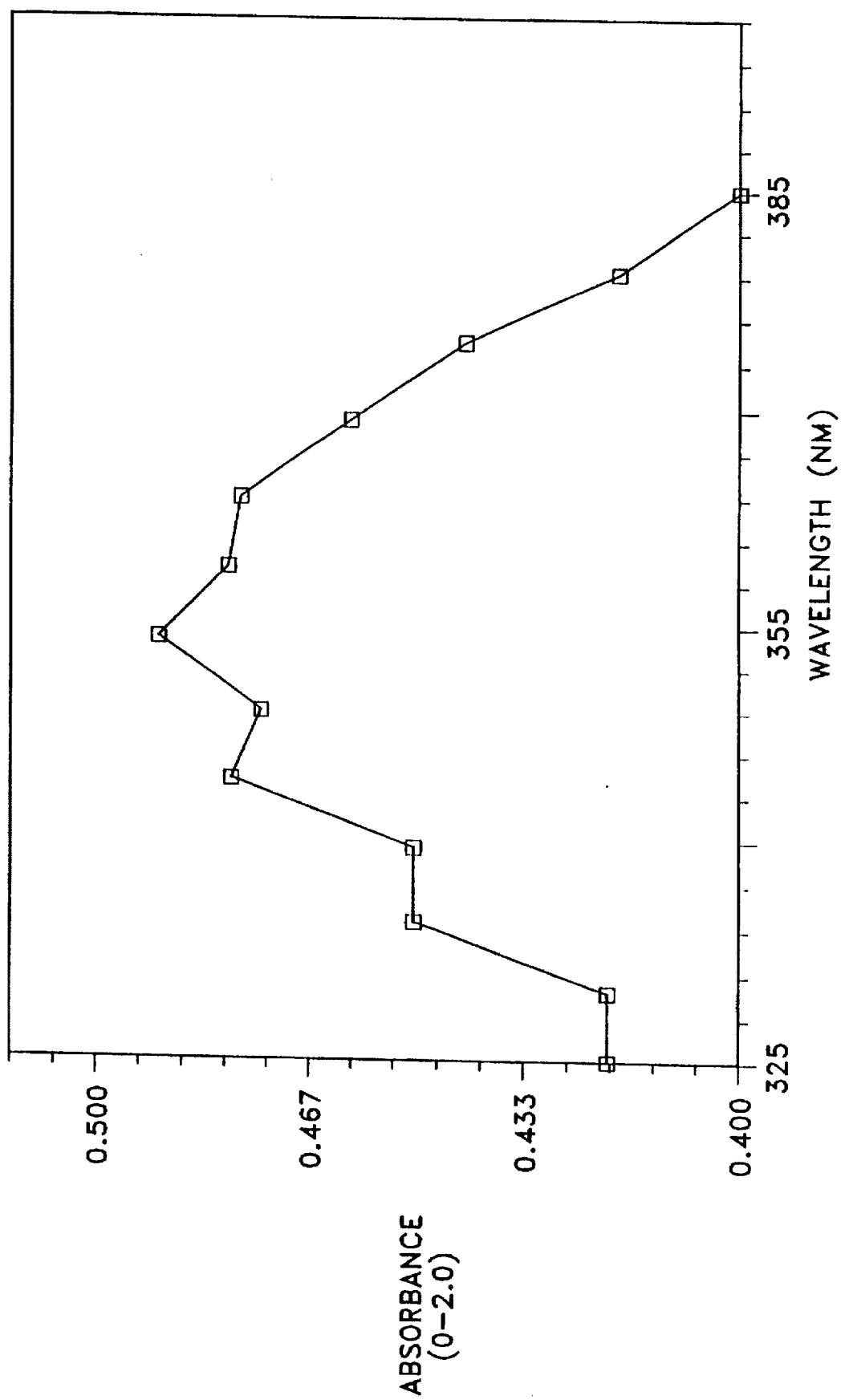
FIG. 2H shows an ultraviolet spectra of bis(thiamine-HCl)Pd at a concentration of $5 \times 10^{-}$4M.
Figure 2I:
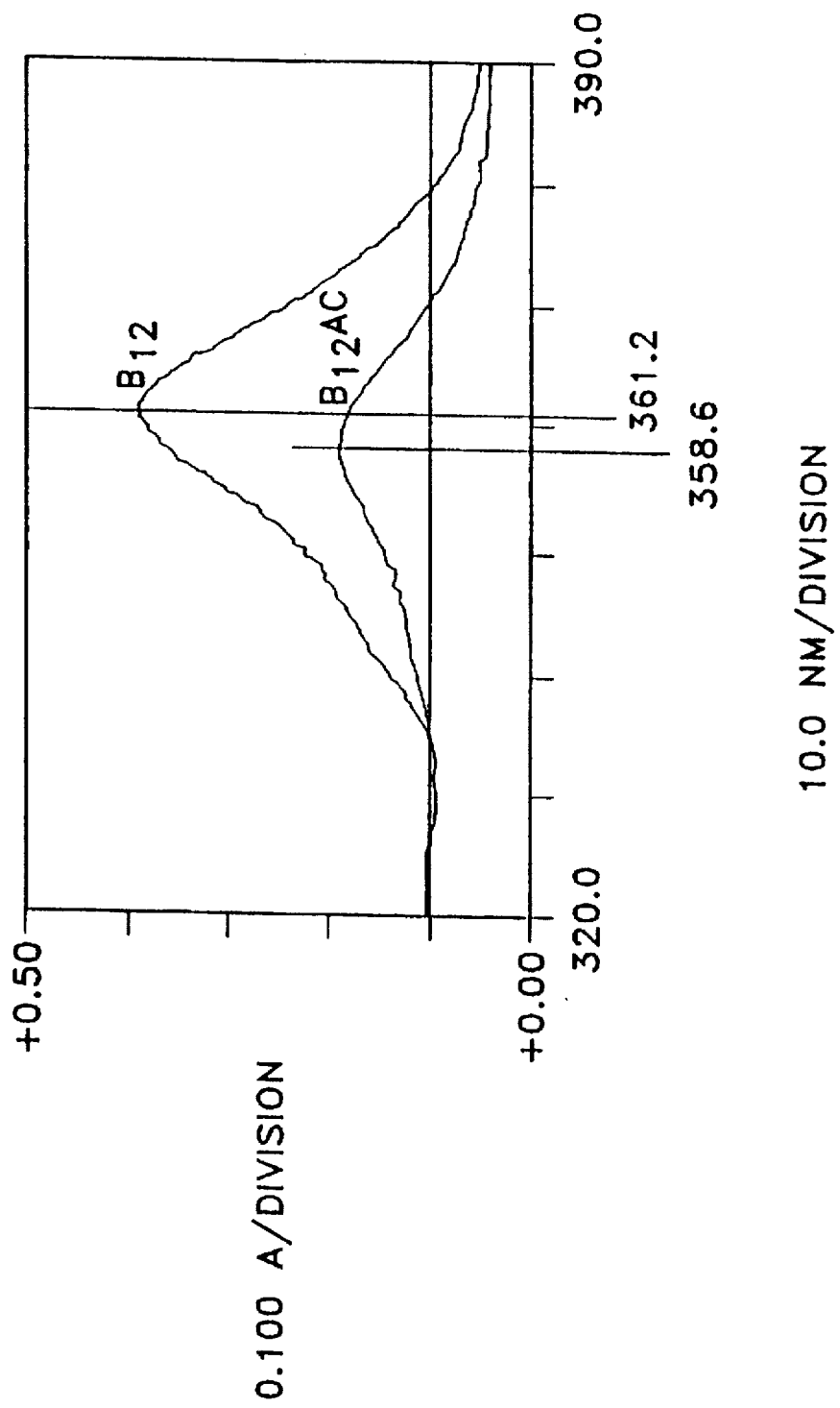
FIG. 2I illustrates a comparison of the ultraviolet spectra of vitamin $B_{12}$ with the activated derivative of vitamin $B_{12}$ at a concentration of $1.5 \times 10^{-5}$M in an experiment conducted May 21, 1993. The reference peak of $B_{12}$ is at 361.2 nm and 0.042 A and the reference peak of $B_{12}Ac$ is at 358.6 nm and 0.044 A.

As can be seen in FIG. 2H, the peak absorbance of bis(thiamine HCl)Pd is 355 nm. For this spectra, a $5\times10^{-4}\mu$ solution was used. FIG. 2I compares the spectra of vitamin $B_{12}$ and the activated cofactor thereof which is included in the $B_{12}$AC-Poly-R2 of the present invention.

For the Pd-lipoic complex of the present invention, the molecular weight for a 1:1 ratio was calculated to be 312.73, although the possibility of polymers of this structure exists, e.g., X(1:1). At a wavelength of 261 nm the absorptivity of the complex (a=A/bc) was $1.1\times10^5$. The molar absorptivity ($\epsilon$=a×mol. wt.) was calculated to be $3.44\times10^7$.

Example 5

Structure of the Palladium-Lipoic Acid Complex

The structure of the palladium-lipoic acid complex was studied by Fourier transform-infra red spectroscopy (FTIR). To perform this study, the red solution containing the essential core complex of palladium-lipoic acid, i.e., Poly-RC, was evaporated to a stable weight residue by heating the solution in a vacuum. The residue was first mixed with KBr and compressed to a tablet and was then scanned in a Perkin-Elmer FTIR spectrophotometer.

Figure 3A:
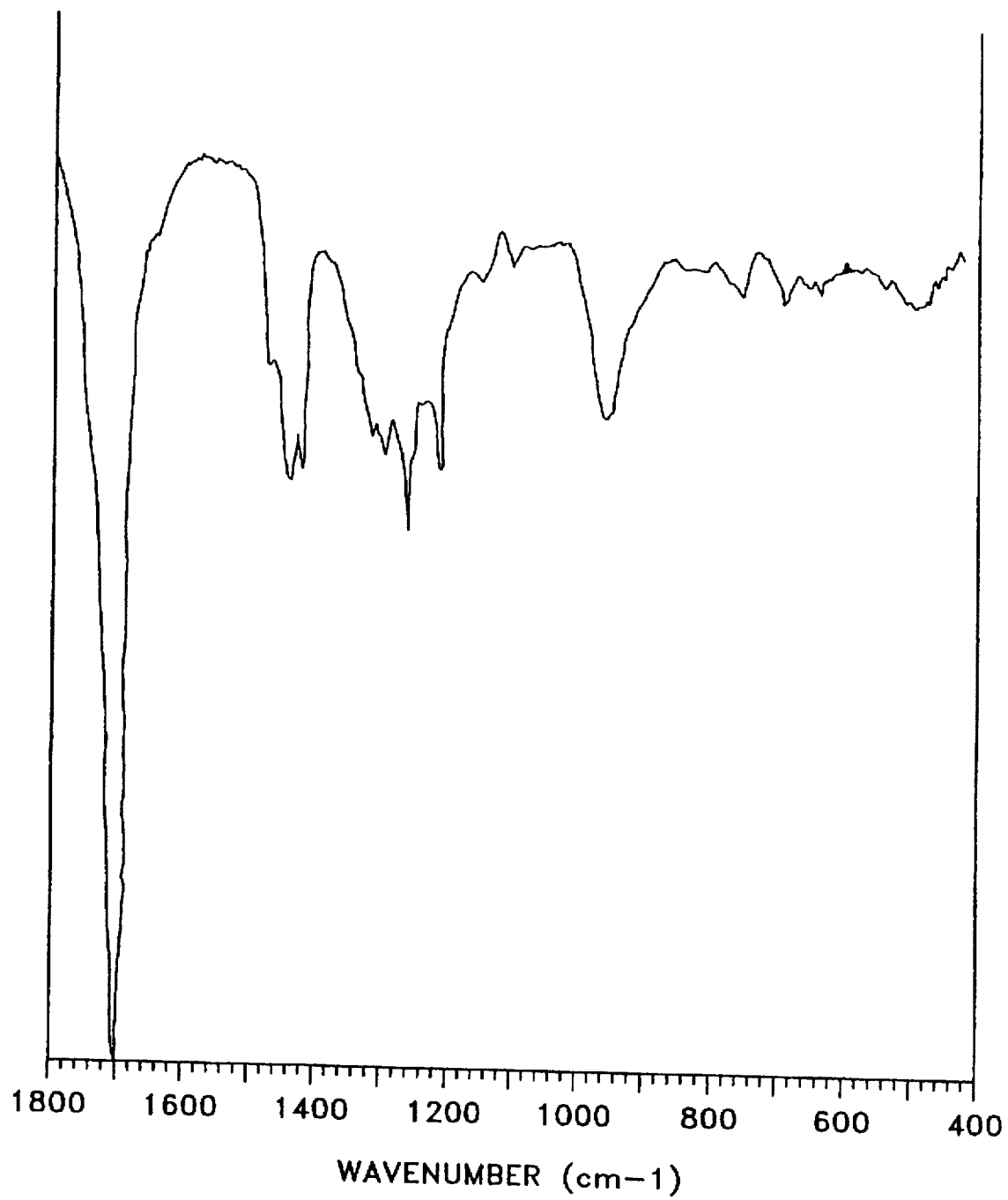
FIG. 3A shows an FTIR scan of Pd-lipoic acid in KBr Mull in an experiment dated 17 Dec. 92.
Figure 3B:
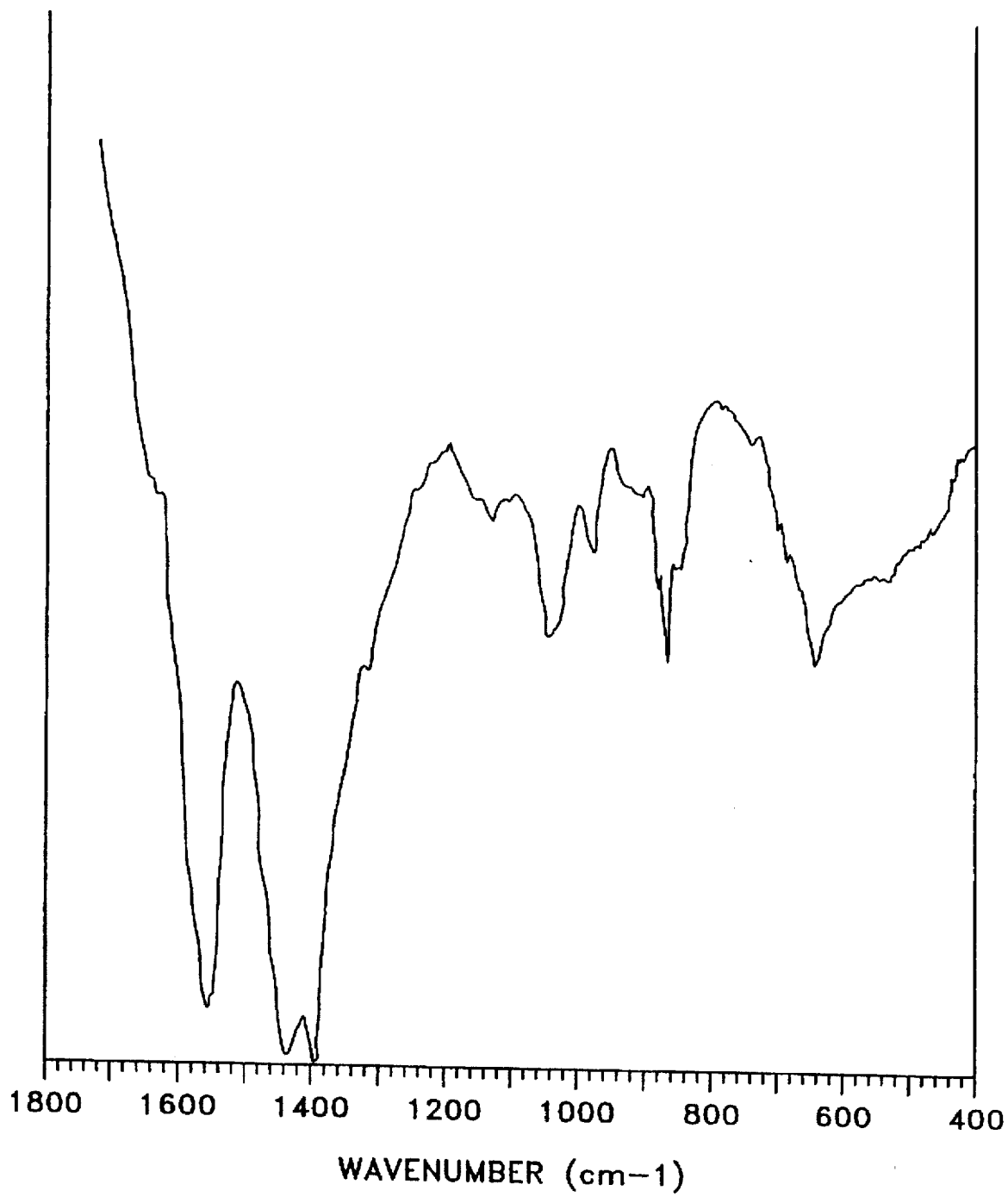
FIG. 3B shows an FTIR scan of Pd-lipoic acid complex in KBr Mull in an experiment dated 17 Dec. 92.
Figure 3C:
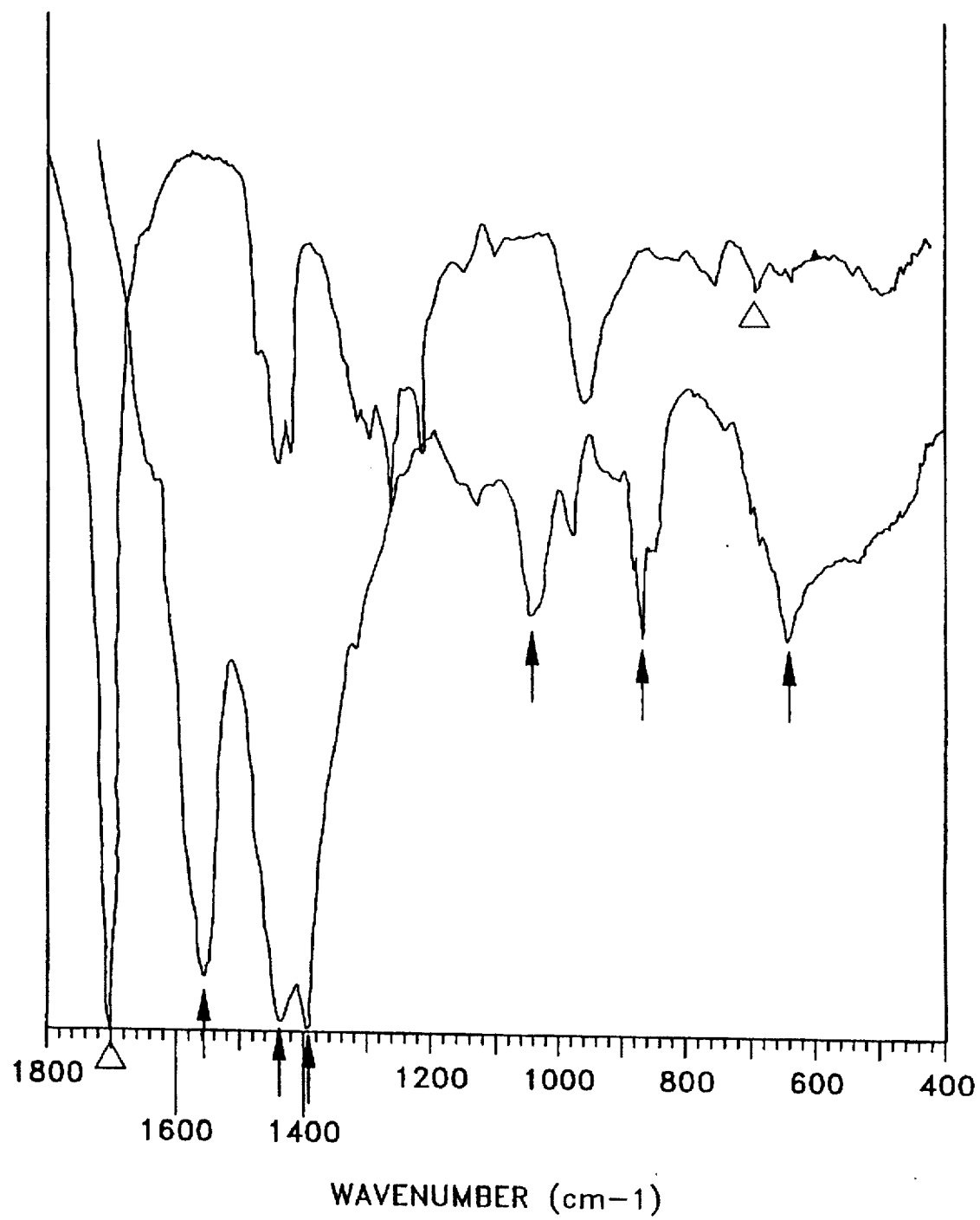
FIG. 3C compares the FTIR scan of Pd-lipoic acid complex and that of lipoic acid in experiments dated 17 Dec. 92.

Uncomplexed lipoic acid was similarly treated. The two FTIR scans are compared in FIGS. 3A, 3B and 3C. Characteristic frequencies of the new complex are marked with arrows. Contributing frequencies of lipoic acid are marked with triangles in the figures.

There were interactions showing changes at six frequencies. The new peaks (cm⁻) were interpreted according to Nakamoto, *Infrared and Raman Spectra of Inorganic and Coordination Compounds*, 4th, John Wiley & Sons (1986); Silverstein et al., *Spectrometric Identification of Organic Compounds*, 3d, John Wiley & Sons (1974); Flett, *Physical Aids to the Organic Chemist*, Elsevier, NY, 162–163 (1962); Schotte, L., "Spectrochemical Studies on Disulphides, 1. An Investigation of Some Linear and Cyclic Carboxylic Substituted Disulphides with Special Reference to the 1,2 Dithiolane System," *Ark. Kemi*, Vol. 8,No. 56, p. 579–596, (1955); and Schotte, L., "Studies on Sulphur Compounds Related to Glutaric and Pimelic Acid with Special Reference to the 1,2-Dithiolane System," *Ark. Kemi*, Vol. 9,No. 37, pp. 441–469 (1956), and were as follows:

645=sulfide stretch, presumably to the metal

865=—$CH_2$ deformation, consistent with chain bend

1040=S-0 stretch,

1420=C-0 stretch, presumably oxygen to metal, also $CH_2$ bend

1440=C-0 stretch, presumably oxygen to metal, also $CH_2$ bend

1575=C-0 stretch, presumably oxygen to metal

The contributing IR frequencies from the spectra of free lipoic acid are as follows:

1700=COO⁻, and C=O 1430 and 1410=$CH_2$ scissor or bend, also C—O symmetric stretch 930=C—C stretch 730 and 680=C—S stretch 480=S—S stretch 1350 and 1250=$CH_2$ twist A depiction of this structure is shown, together with the variant having two lipoic acid moieties, on page 9.

According to the infra-red spectra, the complex between palladium and lipoic acid is bonded: (1) at the carbonyl of the carboxyl group with probable resonance involvement of both oxygens, and (2) at one or more sulfur atoms. In addition, there was a steric assistance by lipoic molecular bending favored by the sulfur to oxygen stretch. Bending was also indicated by the —$CH_2$ deformation.

The result is a bent chain of lipoic acid, with its ends bonded by way of palladium coordination. This 1:1 structure is represented as a bent cyclic structure as previously illustrated. A 1:2 palladium to lipoic acid complex is also possible as illustrated. Crystallographic studies show that the palladium-lipoic acid complexes form trigonal prisms as shown in FIG. 1. Since redox reactions involving the Pd-lipoic acid complex occur, the structure may also be represented by its oxidized and reduced forms, which increases the number of possible structures of the complex.

Example 6

Identification of the Complexes

Figure 4A:
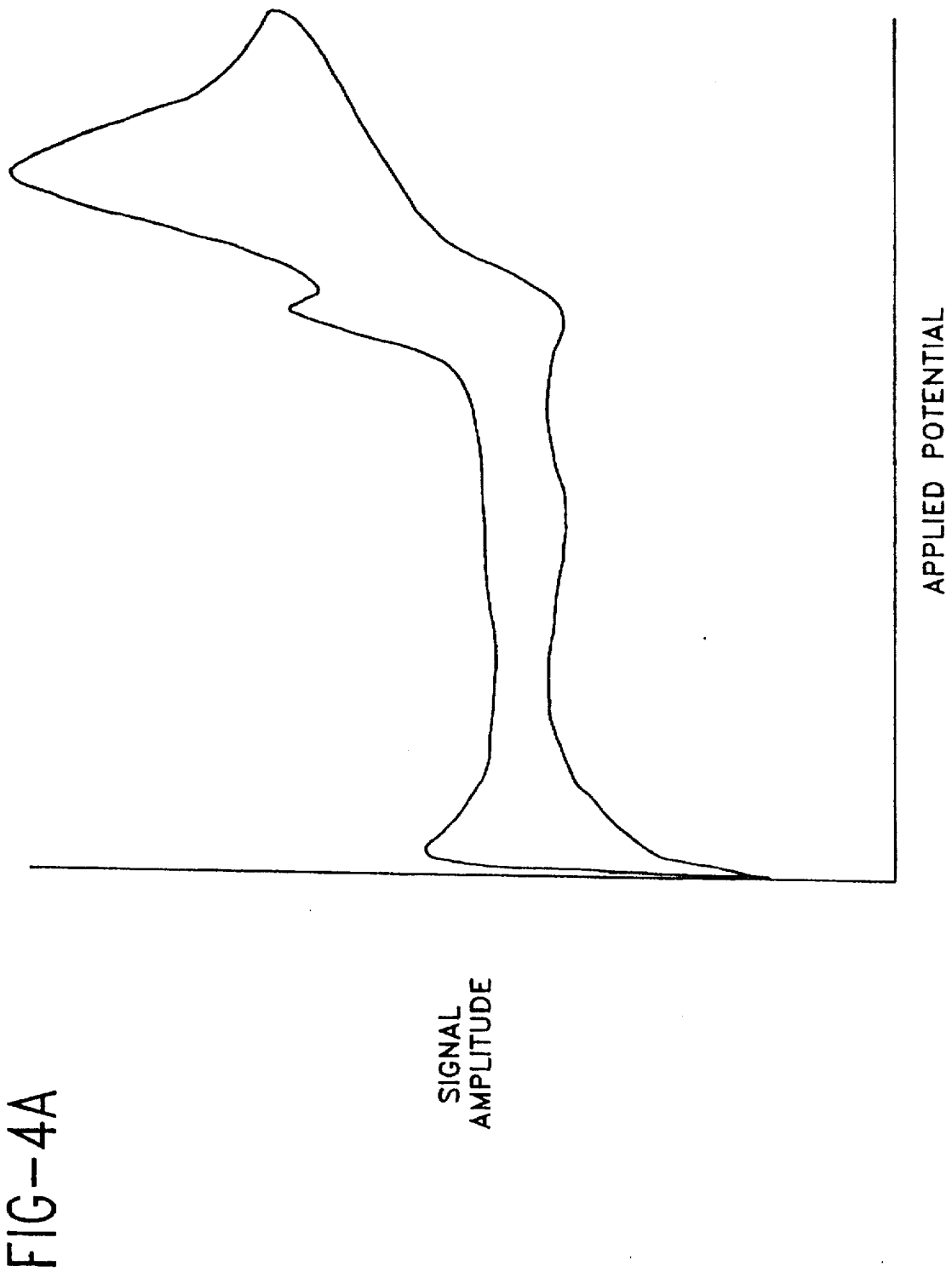
Figure 4B:
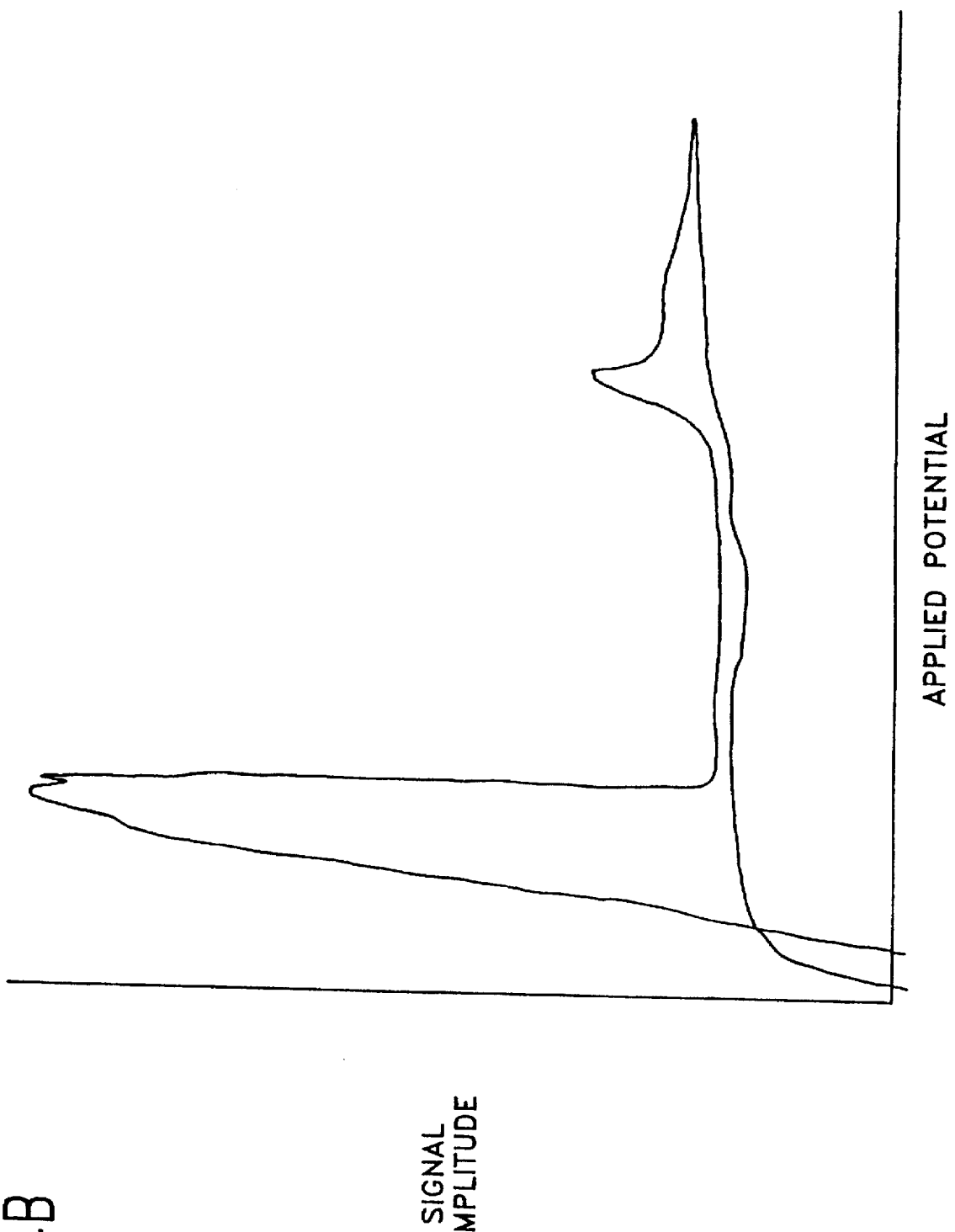
Figure 4C:
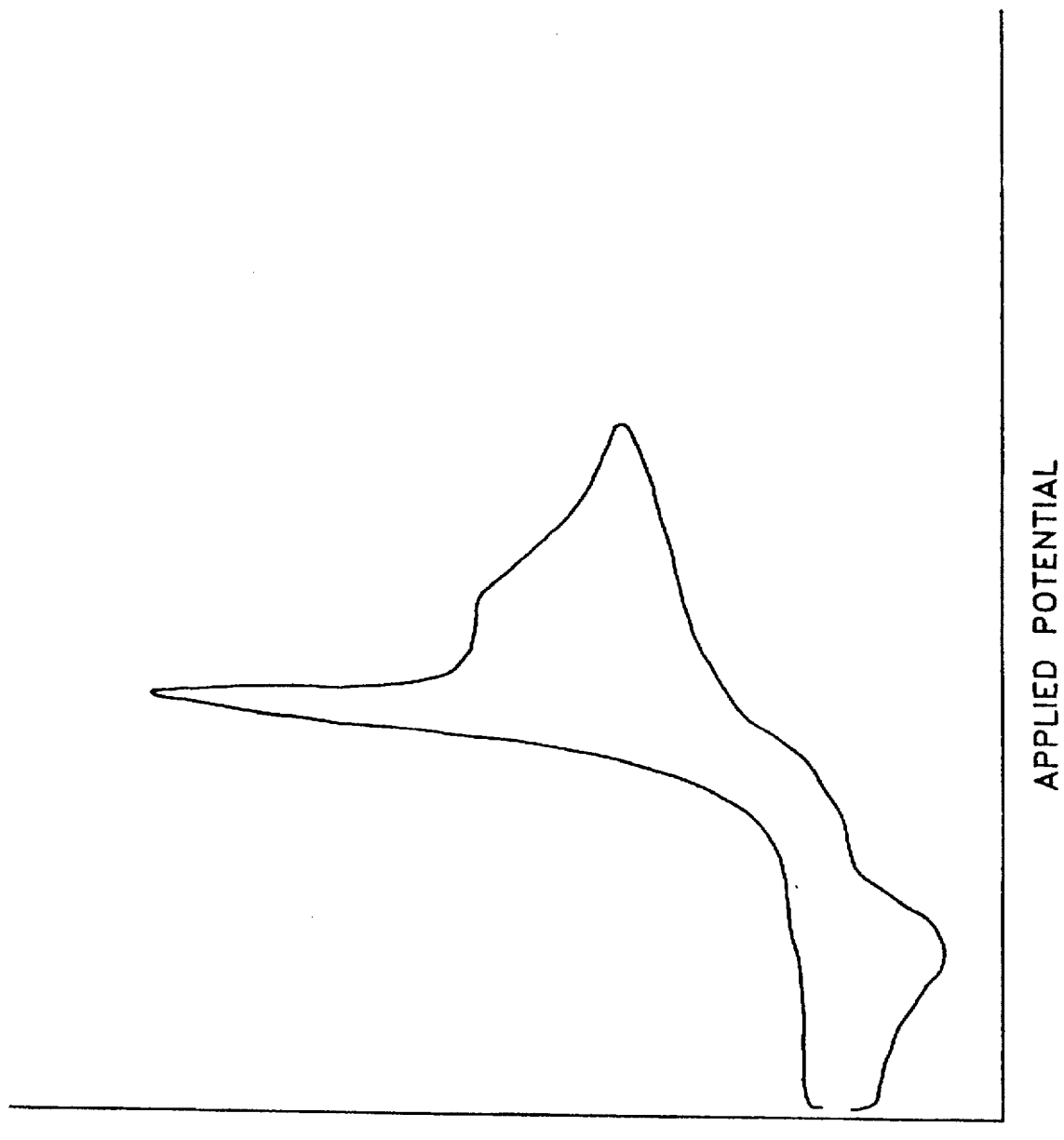

Voltammetry was also used to identify the complexes of the present invention. Cyclic voltammetry of the reductases was performed on an EG&G model 264A polarographic system as follows:

The working electrode used a static mercury drop, the reference electrode was Ag/AgCl wire in KCl solution housed behind a porous Vycor frit and the counter electrode was Ag/AgCl wire. A reversing scan was performed from either 0 or –0.3 Volt to –1.0 Volts at 20 uA or 100 uA sensitivity and a scan rate of 100 mv/sec. Before the reductase sample was run, 9.0 ml of acetate buffer background electrolyte at pH 5.0 was purged for 8 minutes by vigorous bubbling of nitrogen. The addition of each sample was followed by two minutes of nitrogen purging. FIGS. 4A, 4B and 4C show the resulting cyclic voltammetric scans of Poly-RC and Poly-R2. FIG. 4A shows the resulting cyclic voltammetric scan of Poly-RC (0.12μ) from 0 to –1.0 volts at 100 μA sensitivity. FIG. 4B shows the scan of Poly-R2 (0.08 1) from 0 to –1.0 volts at 100 μA sensitivity. FIG. 4C shows the scan of Poly-R (0.08μ) from –0.3 to –1.0 volts at 20 μA sensitivity.

The scans were quasi-reversible with proportionally undersized anodic peaks. Cathodic peaks with a common base typifying catalytic activity were characteristic of the reductases. FIG. 4A shows peaks in Poly-RC at –660 and –800 mv. In FIG. 4B, with slightly different parameters, Poly-R2 had an enormous catalytic triple peak at –160, –200, and –218 mv. This was due to the addition of thiamine-HCl and was recorded at 100 uA sensitivity. The remaining two peaks were at –718 and –800 mv and are shown in FIG. 4B, and then more graphically in FIG. 4C at 20 uA sensitivity. FIGS. 4E and 4F illustrate the electrochemical signatures for $B_{12}$AC-Poly-R2 (0.04μ). The peaks for this complex were at –150, –200, –220, –705 and –845 mv and are shown in FIG. 4E from –0.3 to –1.0 volts at 100 uA sensitivity, and then more graphically in FIG. 4F from 0 to –1.0 volts at 20 uA sensitivity.

These scans in FIGS. 4A, 4B, 4C, 4E and 4F thus represent the identifying electrochemical signatures of these novel compounds of the present invention. In addition to characteristic reactions of these reductases with nucleic acids, the electrochemical signatures allow identification of the novel polynucleotide reductases of the present invention.

Figure 4D:
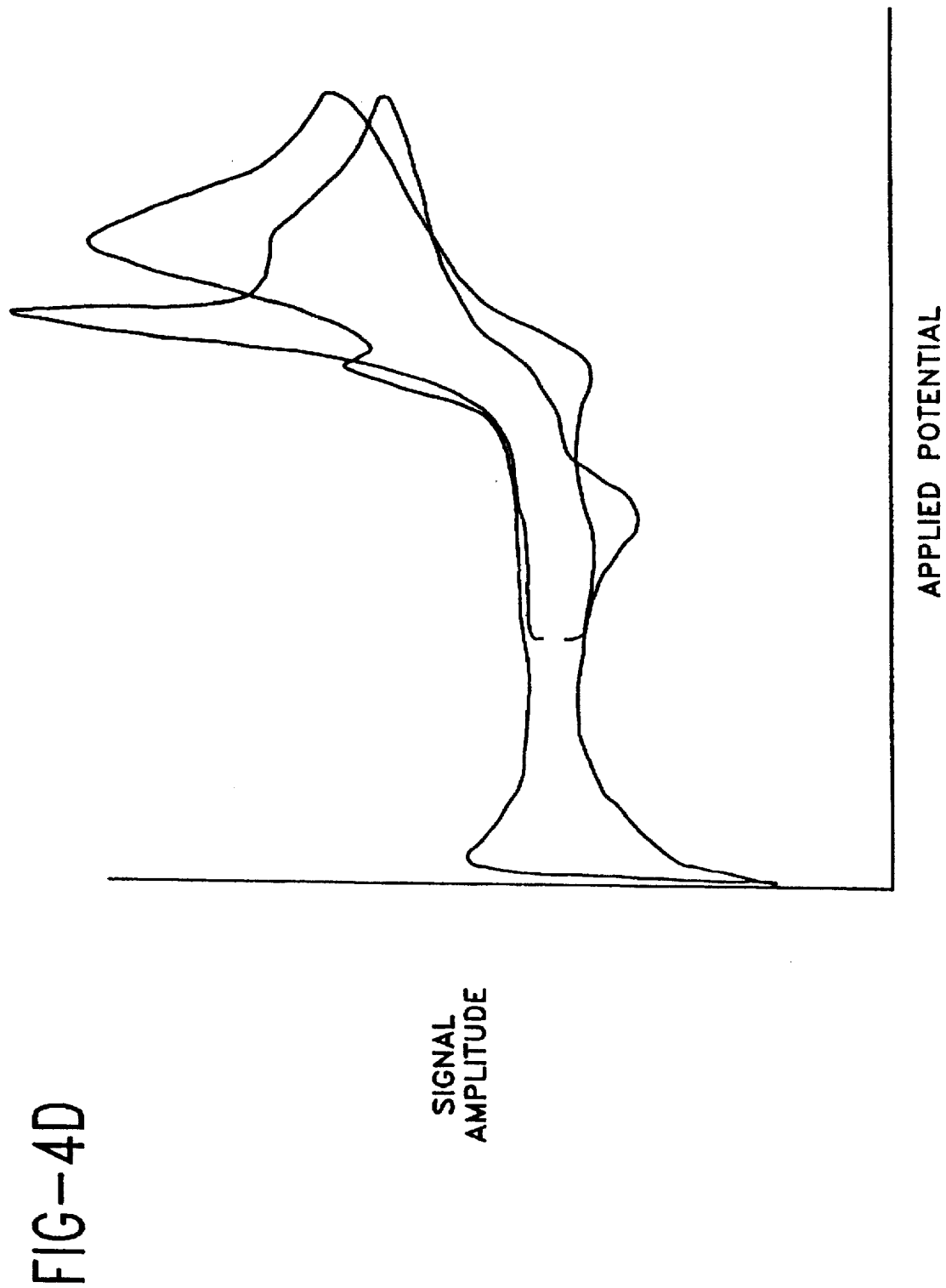
Figure 4E:
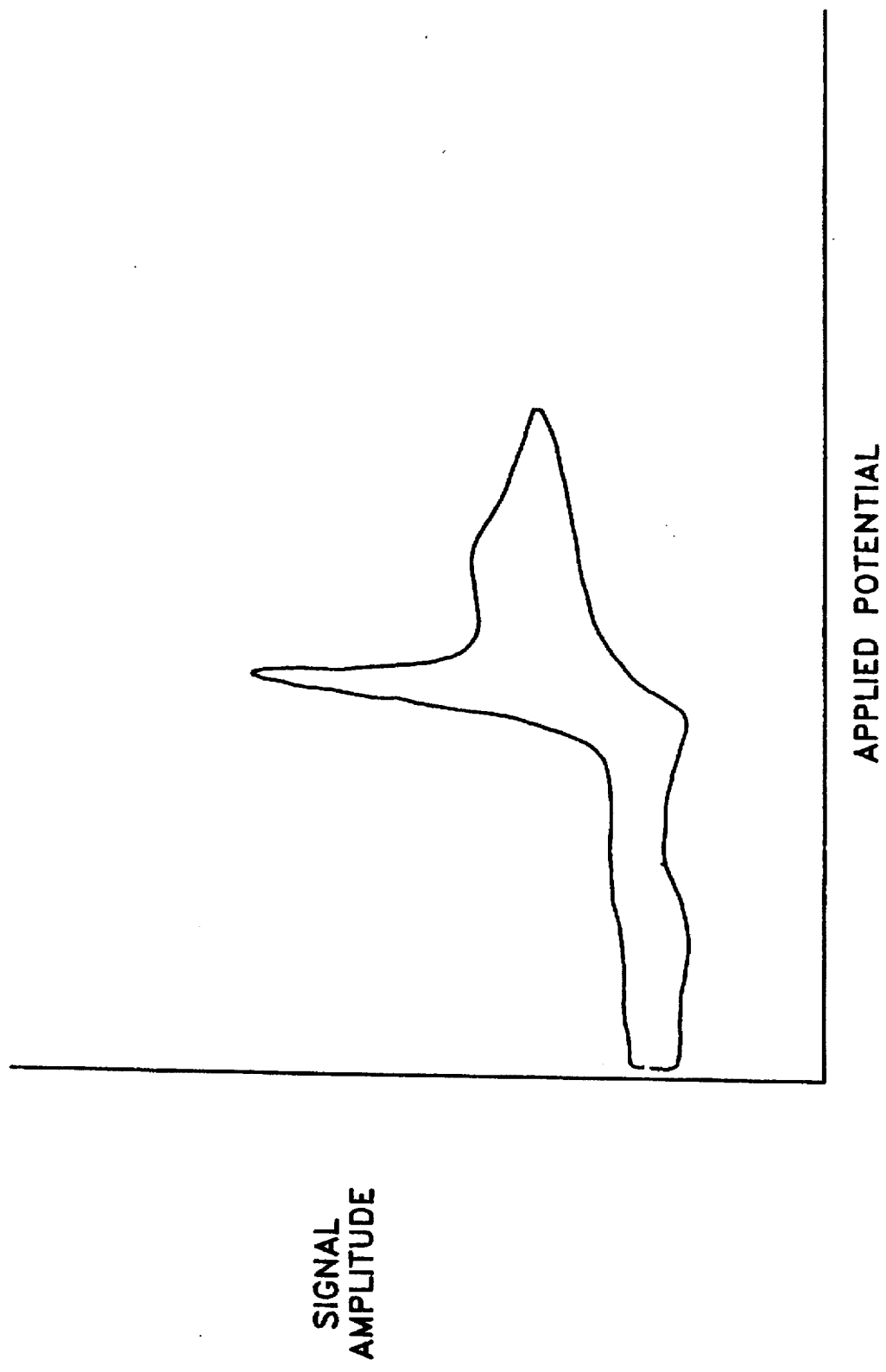
FIGS. 4E and 4F illustrate cyclic voltammetric scans of the activated $B_{12}$-Poly-R2 complex.
Figure 4F:
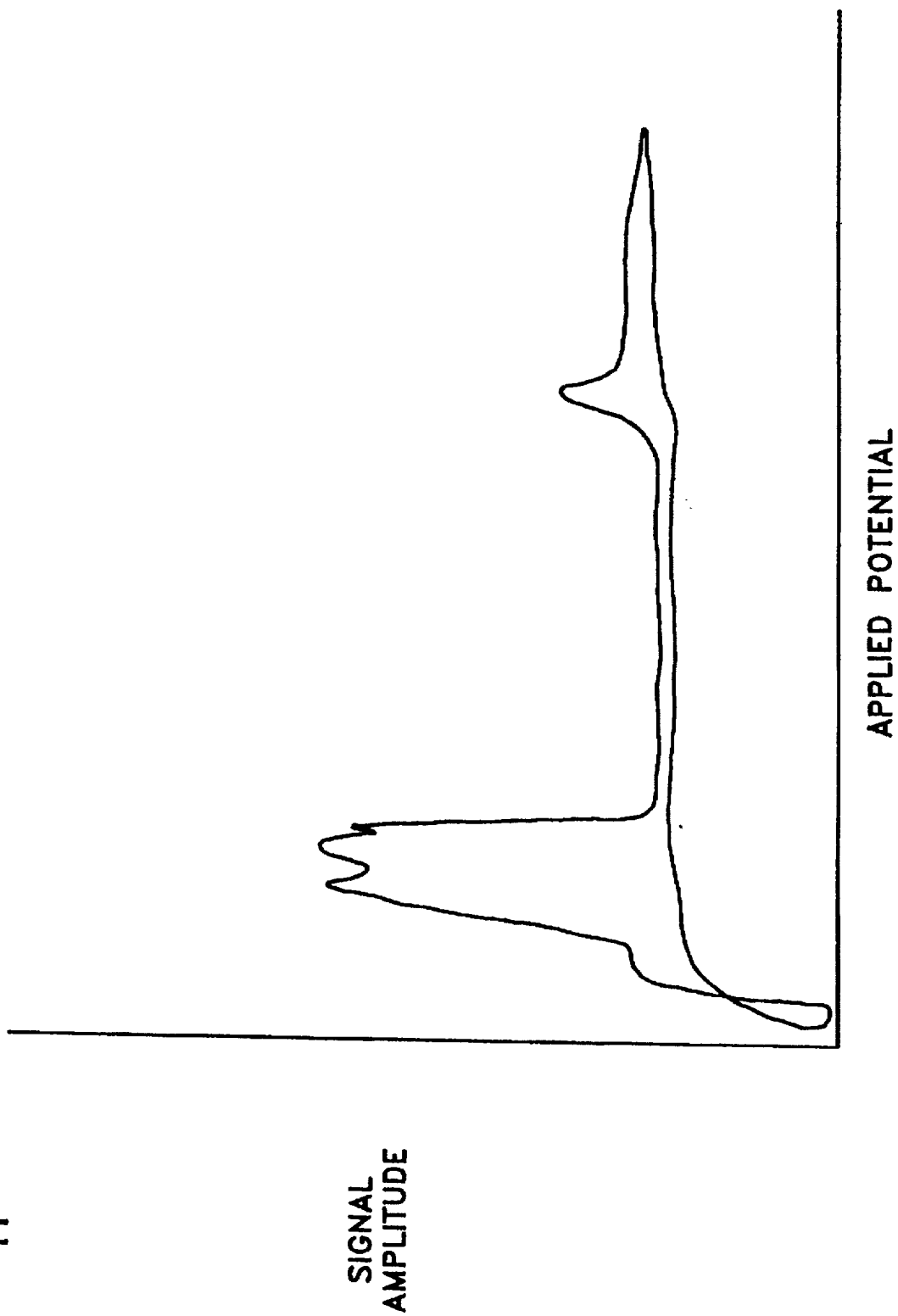

With respect to the interaction between palladium and thiamine, these materials act as a redox pair which shifts the peaks of Poly-RC as measured by voltammetry to form the new Poly-R2 peak at –718 mv as is shown in FIG. 4D.

Example 7

Charge Interactions of DNA Reductases

Figure 5:
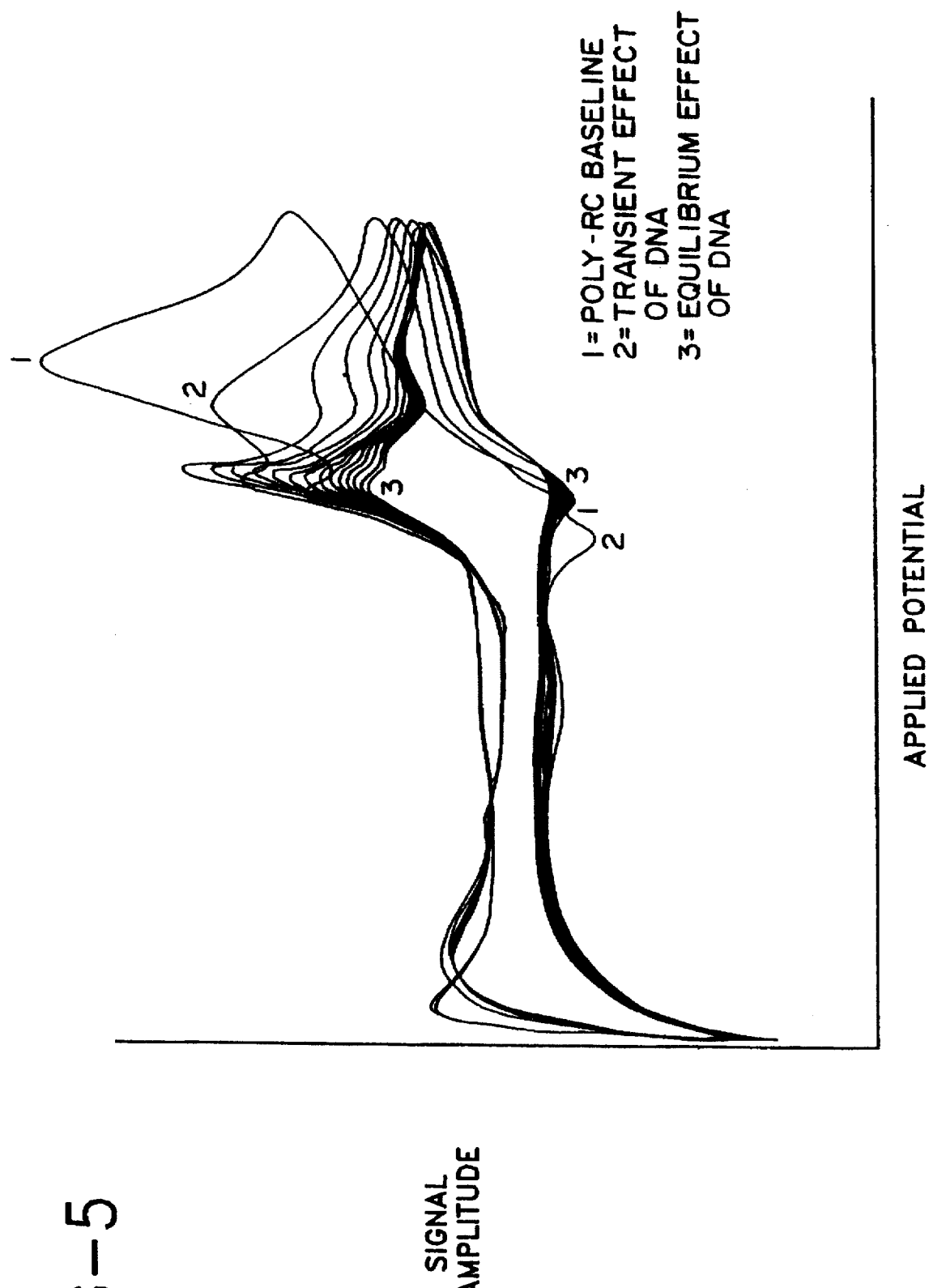

To demonstrate the charge interactions of DNA reductases, cyclic voltammetry was performed on the interactions of the Pd-lipoic acid reductases with DNA or RNA. FIG. 5 shows the charge interaction of Poly-RC with DNA. DNA has no electro-chemical signal of its own in this range. In this example, 1.0 ml of a 5 mg/ml DNA solution was added to 250 μl of a 0.12μ Poly-RC solution. In this voltammetric study the Poly-RC baseline (1), the transient effect of the addition of DNA on the baseline (2), and the equilibrium effect of the addition of DNA (3) were evident. The double peaked catalytic wave of Poly-RC was altered on the addition of DNA. This scan was run from 0 to –1.0 volts at 20 μA sensitivity.

The more reduced (–) peak became diminished and the more oxidized (+) peak became transiently increased, and was further decreased when equilibrium was reached. Thus current had dropped and voltage had moved in the oxidative direction.

These voltammetry studies, therefore, showed that DNA had acted as an oxidant. The amount of energy transferred is calculated from the shift in the voltage and current coordinates in terms of the Nernst relation. This interpretation of shifts in electro-potential curves follows the interpretations of electrochemistry literature, e.g., Maloy, "Factors Affecting the Shape of Current Potential Curves," *J. Chem. Ed.*, 60(4):285–289 (April 1983); Rieger, *Electrochemistry*, Prentice Hall (1987); and Riley et al., *Principles of Electroanalytical Methods*, John Wiley (1987).

Figure 6A:
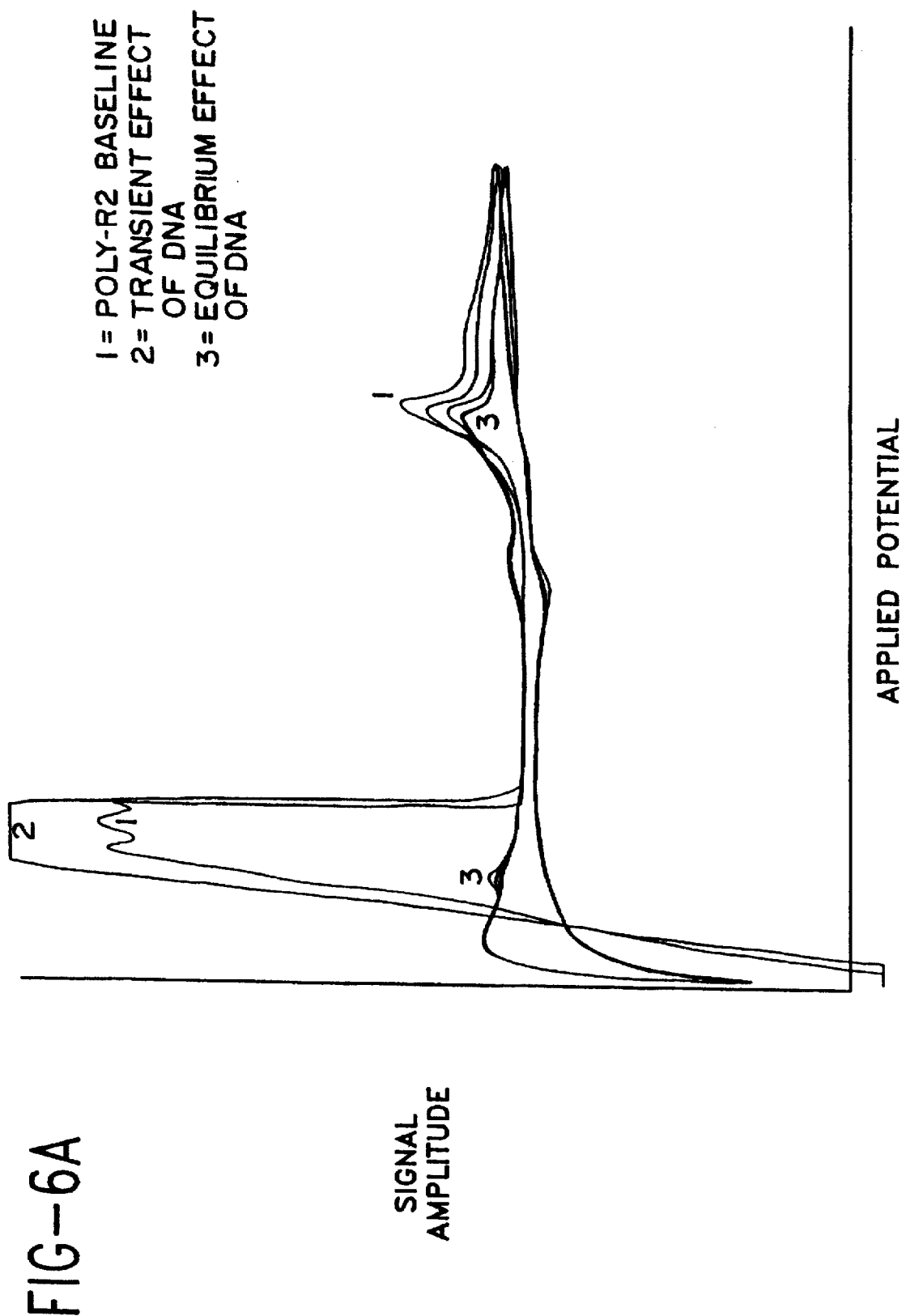
FIGS. 6A and 6B illustrate cyclic voltammetry patterns for Poly-R2 interaction with DNA.
Figure 6B:
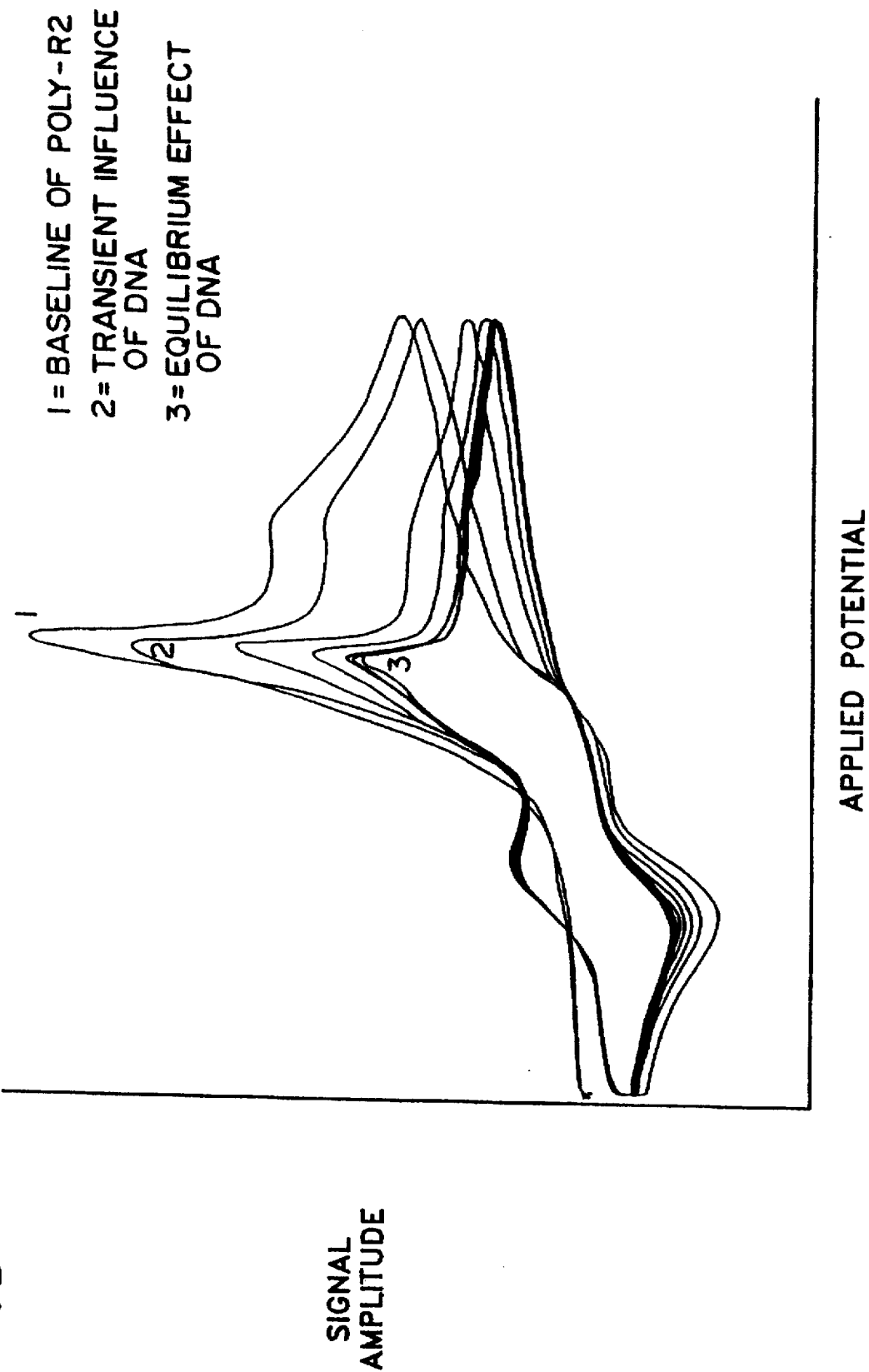

FIGS. 6A and 6B show a similar pattern for Poly-2( interaction with DNA. FIG. 6A was run from 0 to –1.0 volts at 100 μA sensitivity, while FIG. 6B was run from –0.3 to –1.0 volts at 20 μA sensitivity. In both figures the Poly-R baseline (1), the transient effect of the DNA (2), and the equilibrium effect of the DNA (3) were evident. 1.0 ml of a 5 mg/ml DNA solution was added to 0.3 ml of a 0.08μPoly-R2 solution. DNA again acted to suppress current peaks and shift the voltage in the (+) direction. For Poly-2 the shifts were of greater magnitude. FIG. 6C shows another similar pattern of reaction for Poly-R2 (0.3 ml of a 0.08μ solution) and yeast RNA (1.0 ml of a 5 mg/ml solution) with a scan from –0.3 to –1.0 volts at 20 μA sensitivity. In this figure (1) represents the Poly-R2 peak. These figures thus evidence that Poly-R can reduce both DNA and RNA.

Figure 7A:
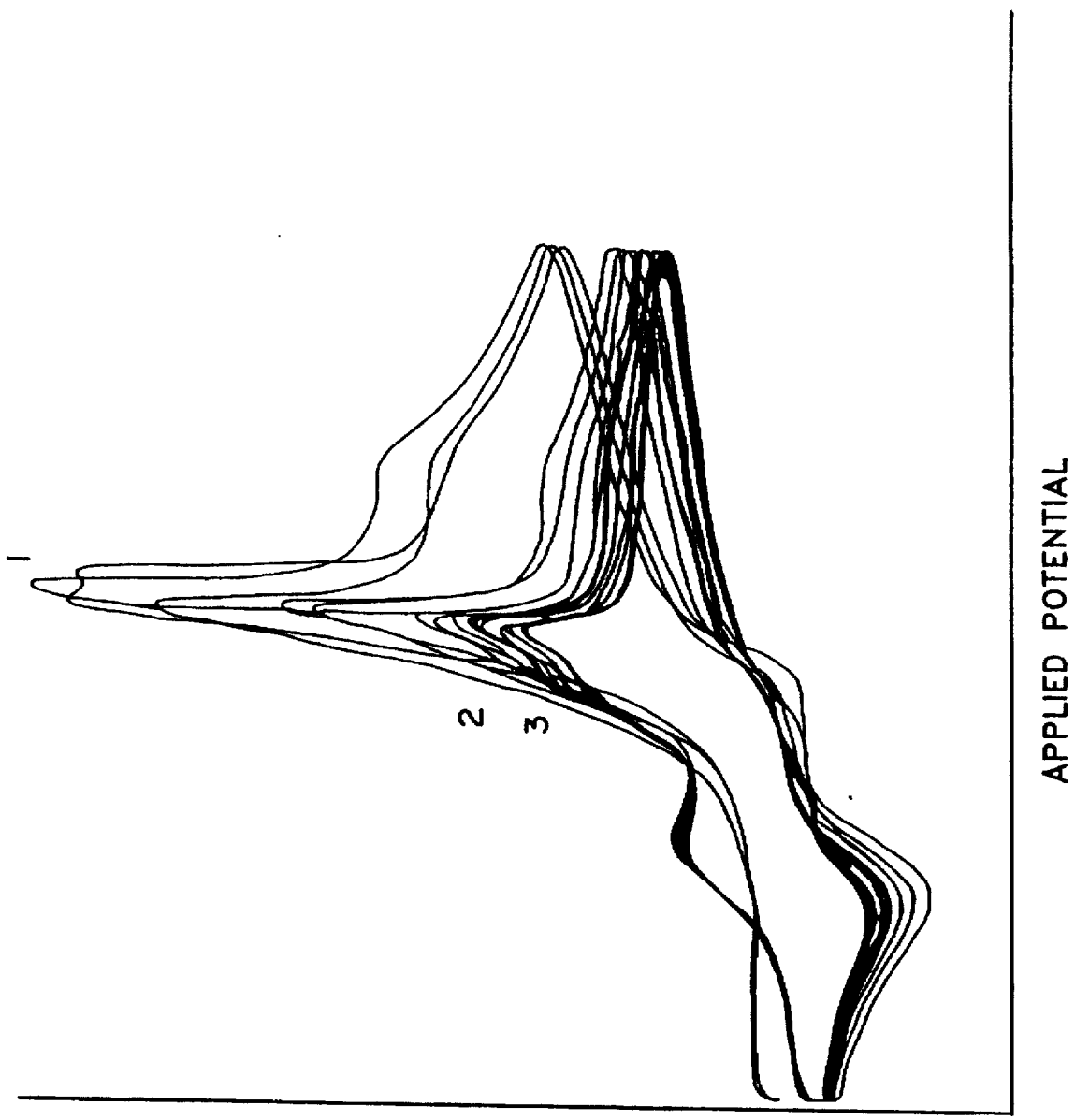
FIG. 7A shows cyclic voltammetry patterns of the interactions of Poly-R2, DNA and vitamin $B_{12}$.
Figure 7B:
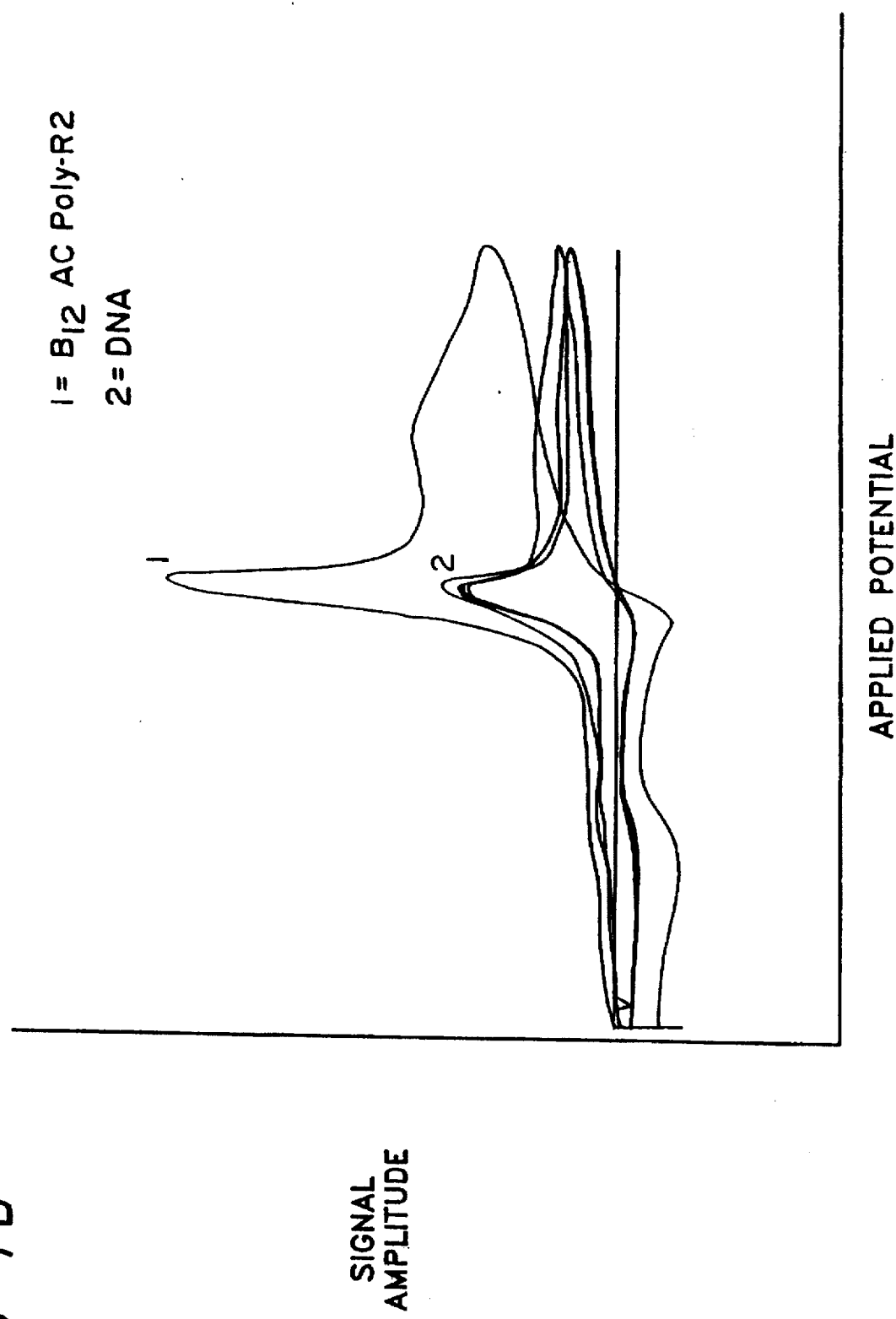

FIG. 7A shows cyclic voltammetry of the interactions of Poly-R2 (0.3 ml of a 0.08μ solution), DNA (1.0 ml of a 5 mg/ml solution) and vitamin $B_{12}$ (cyanocobalamin) (1.0 ml of a 0.2 mg/ml solution). This can be compared to FIG. 7B which shows the interactions of $B_{12}$AC-Poly-R2 (0.5 ml of a 0.04μ solution) with DNA (0.5 ml of a 5 mg/ml solution). Both scans were run from –0.3 to –1.0 volts at 20 μA sensitivity. As can be seen by the two figures, the interaction of Poly-R2 with the activated form of $B_{12}$ and DNA will reach equilibrium much more rapidly than Poly-R2 with vitamin $B_{12}$. In FIG. 7A, the baseline signal marked (1) in the figure was oxidized by DNA to the first equilibrium at (2). At this point, addition of vitamin $B_{12}$ produced a further oxidation which reached equilibrium at (3). In FIG. 7B, the baseline signal marked (1) in the figure was oxidized by DNA to equilibrium at (2). Thus, equilibrium was rapidly achieved. This effect of $B_{12}$ was restricted to DNA, and was not demonstrable in the RNA oxidation of Poly-R2. These data have implications regarding the biochemistry of vitamin $B_{12}$ and suggest its possible role as a hydrogen receptor for DNA. For example, vitamin $B_{12}$ has recently been reported as a radical trap by Finke et al., "Radical Cage Effects in Coenzyme $B_{12}$: Radical Trapping, Product and Kinetic Studies," *J. Inorg. Biochem.*, 51(1 and 2):221 (August 1993).

Example 8

Induction of New Yeast Form

Studies conducted by the present inventor illustrated that polynucleotide reductases induce new varieties of cell forms in amoeba, yeast, and mold. Brewer's yeast (*Saccharomyces cerevisae*) was cultured in 2.0% malt extract and 2.0% sucrose. Poly-R2 was added to achieve a concentration of $10^{-7}$M.

Figure 8A:
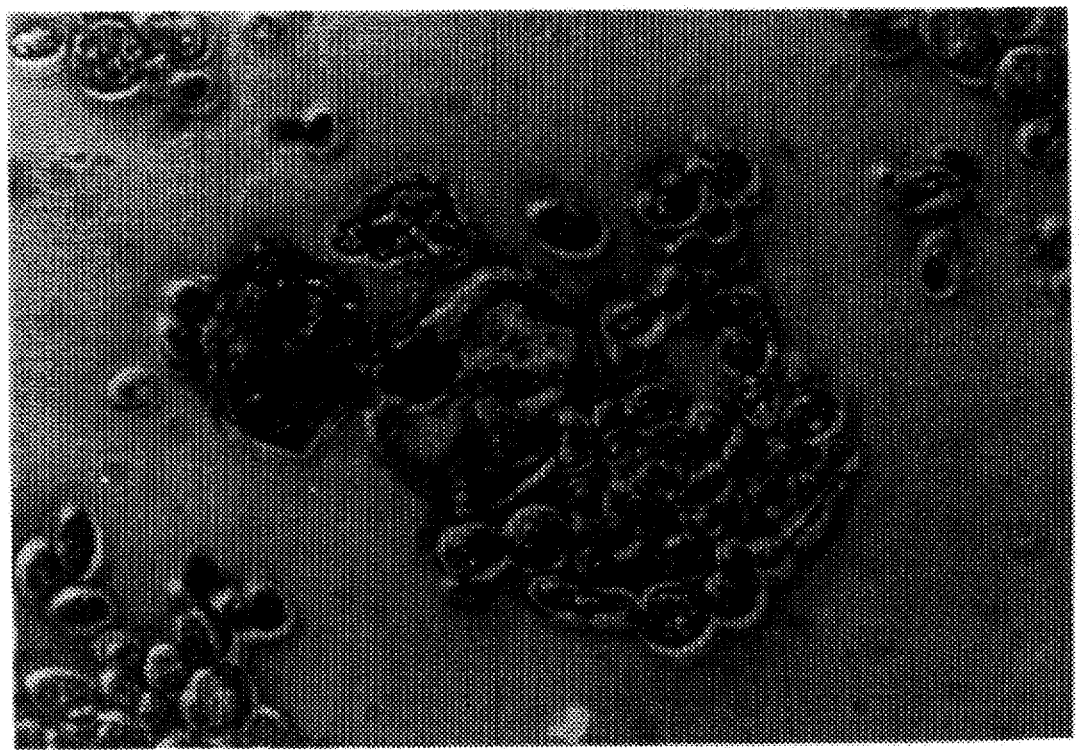
FIG. 8A illustrates induction of giant forms of Baker's yeast by DNA reductase and altered cell morphology of yeast cells to which Poly-R2 was added.
Figure 8B:
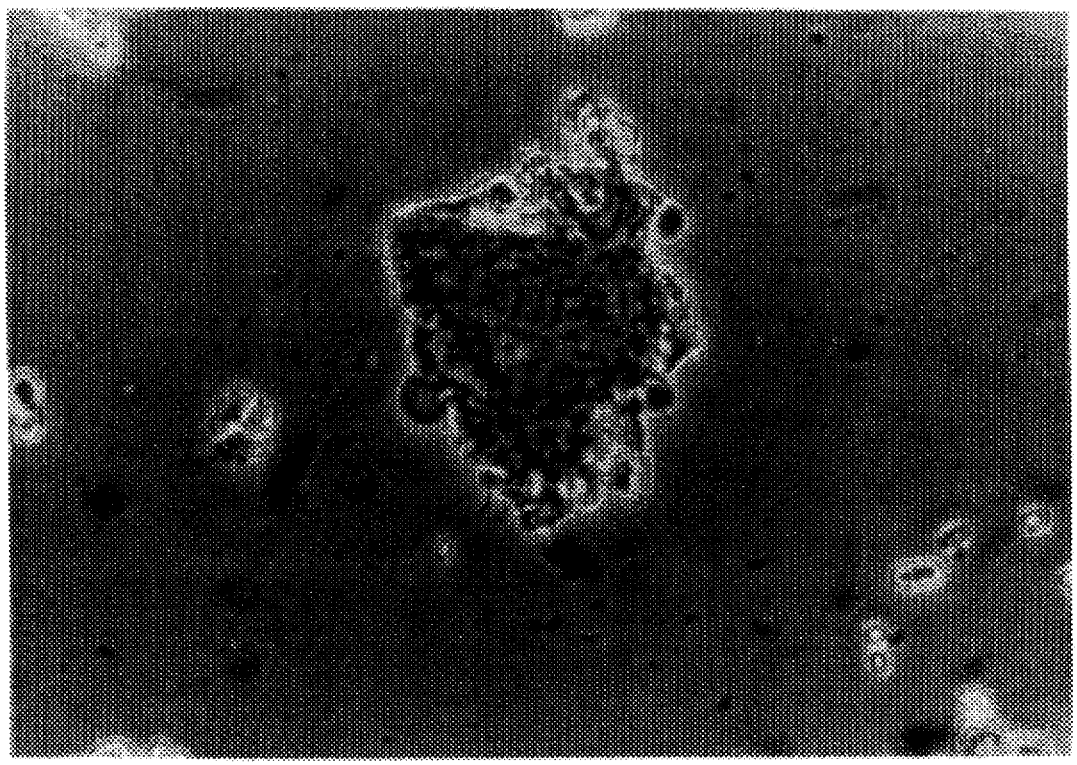
FIG. 8B shows a stage in the giantization of the yeast cells in which lipid drops are lost from the cell.

The yeast was incubated for 30 minutes at 28° C. and examined under phase microscopy. FIG. 8A illustrates the altered cell morphology of the yeast cells. Large flat cells were one kind of new variety produced by the addition of Poly-R2. FIG. 8B shows a stage in the giantization of these cells in which lipid droplets are lost from the cell. The demulsification of lipid may be a result of the loss of membrane charge. This cell variety is not described in the group of letters to Science on the history of yeast morphology found in Witkus, Steensma et al., Berbee et al., *Science*, 257:1610 (Sep. 18, 1992).

Figure 9:
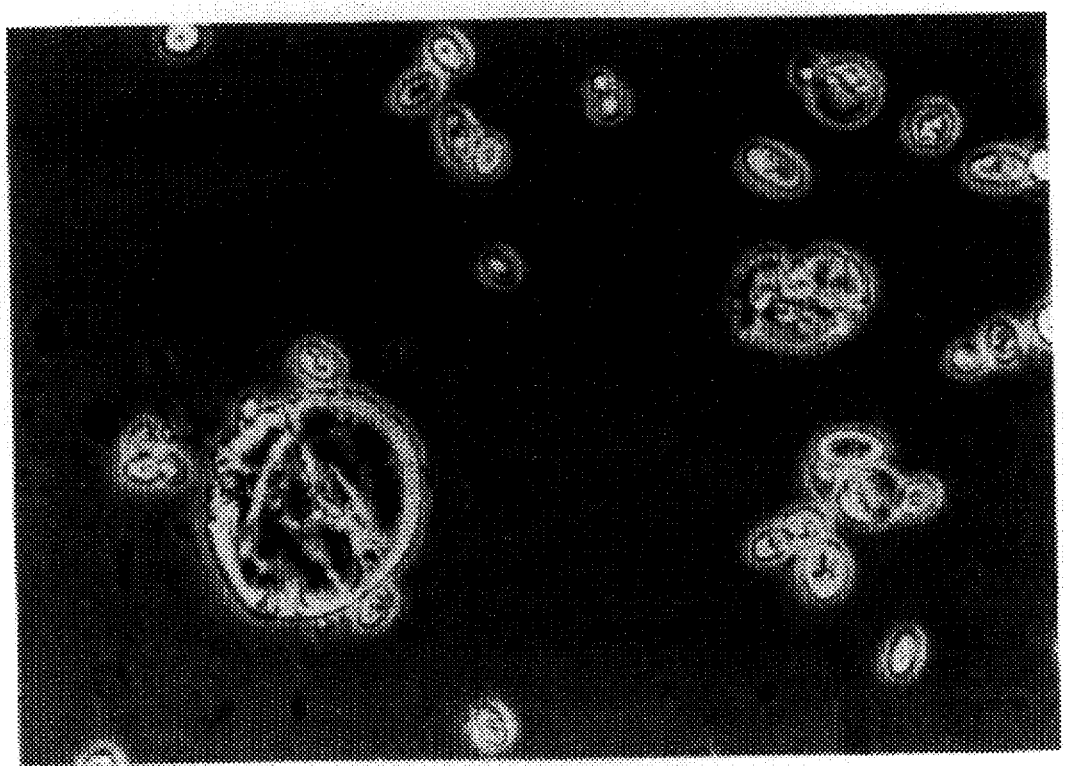
FIG. 9 shows the effect of $B_{12}$ and Poly-R2 on Baker's yeast cells showing cell enlargement with heterochromatin formation.

FIG. 9 shows the effect of vitamin $B_{12}$ and Poly-R2 on Baker's yeast. Exaggerated heterochromatin was produced by the addition of vitamin $B_{12}$ and Poly-R2 to Baker's yeast. In cells that have started to enlarge, there was a dense condensation of chromatin at the nuclear membrane and complete vacuolation of the remaining nuclear region. As can be seen in the figure, some small cells had not yet developed these features.

Example 9

Compassionate Investigational New Drug Study in Humans

Ten individuals having severe psoriasis with thick, large plaques involving greater than 40% of their body surface currently undergoing standard therapy, such as topical steroid, topical tar preparations, ultra violet light treatment, or methotrexate therapy, were chosen for an informal study to investigate the benefits of $B_{12}$AC-Poly-R2 in the treatment of psoriasis.

A particular area, most often the most recalcitrant and thickest accessible plaque on the patient's body, was chosen for treatment. Each patient was given 5 to 10 ml of $B_{12}$AC-Poly-R2 which was applied with a cotton-tipped applicator one to two times daily on the selected area for one week. After the first application, a dramatic decrease in pruritus of the lesion resulted almost immediately. Itching persisted, however, in the untreated lesions. The area of application was also observed by the patients to feel less tight, "less thick" and more supple.

Although one patient reported tightness, dryness and "crustiness" of the treated area a few days after regular twice daily application of the $B_{12}$AC-Poly-R2, these side-effects disappeared when a moisturizer was used by the patient. A reddish-brown stain resulted upon application of the compound of the present invention, which washed off after 2 to 3 days.

Upon continuous topical administration one to two times daily of $B_{12}$AC-Poly-R2 for one week, significant objective improvement of psoriatic lesions were observed. Scaling, thickness, roughness and inflammation of psoriatic plaques were reduced by at least 50%. In some treated areas, the psoriatic plaques were thinned down to a sufficient degree that normal skin markings, e.g., stretch marks and skin creases were again evident in the lesional areas. While no treated plaques have been completely resolved and cleared, these positive therapeutic effects observed after only one week of topical treatment were significant. As of the filing date of this application, six of the ten patients are presently undergoing further treatment with the $B_{12}$AC-Poly-R2 composition of the present invention.

FIGS. 10A, 10B, 10C, 11A, 11B, 12A, 12B, 12C, 13A and 13B illustrate photographs of patients who have received topical treatment of $B_{12}$AC-Poly-R2. As can be seen in these figures, after treatment with $B_{12}$AC-Poly-R2 the treated areas appear smoother and less scaly as compared with the untreated lesions.

Figure 10A:
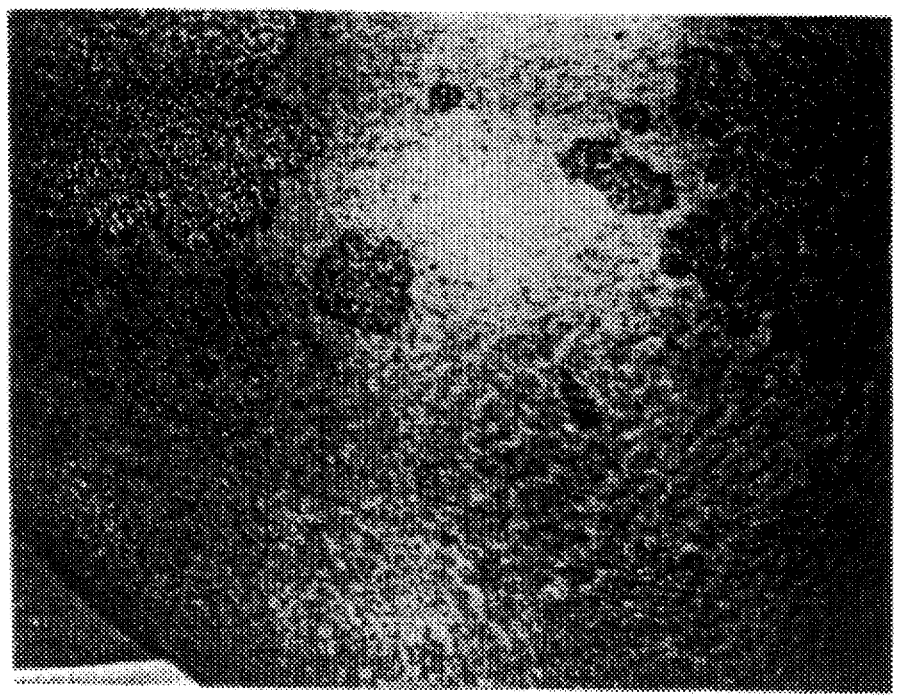
Figure 10B:
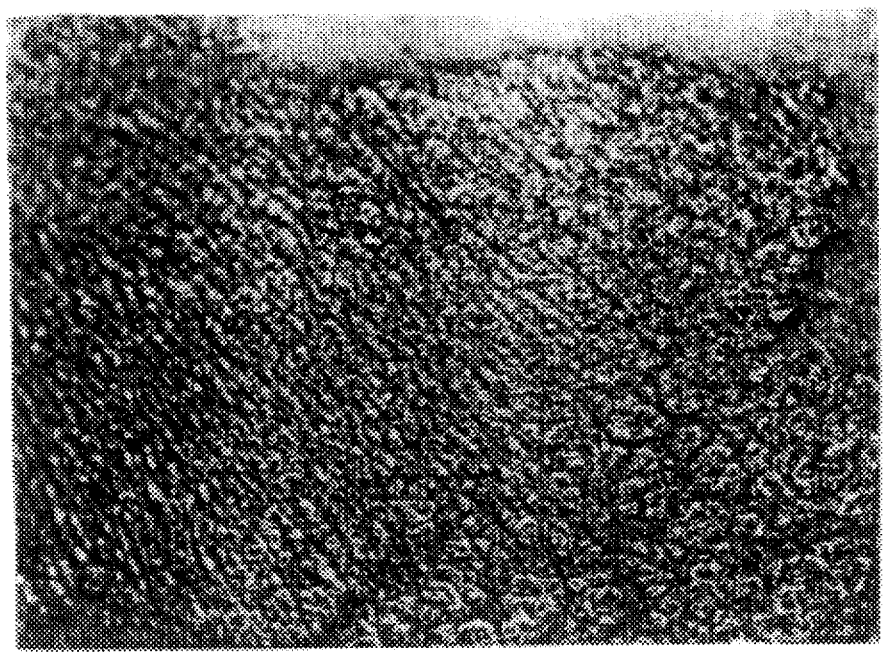
Figure 10C:
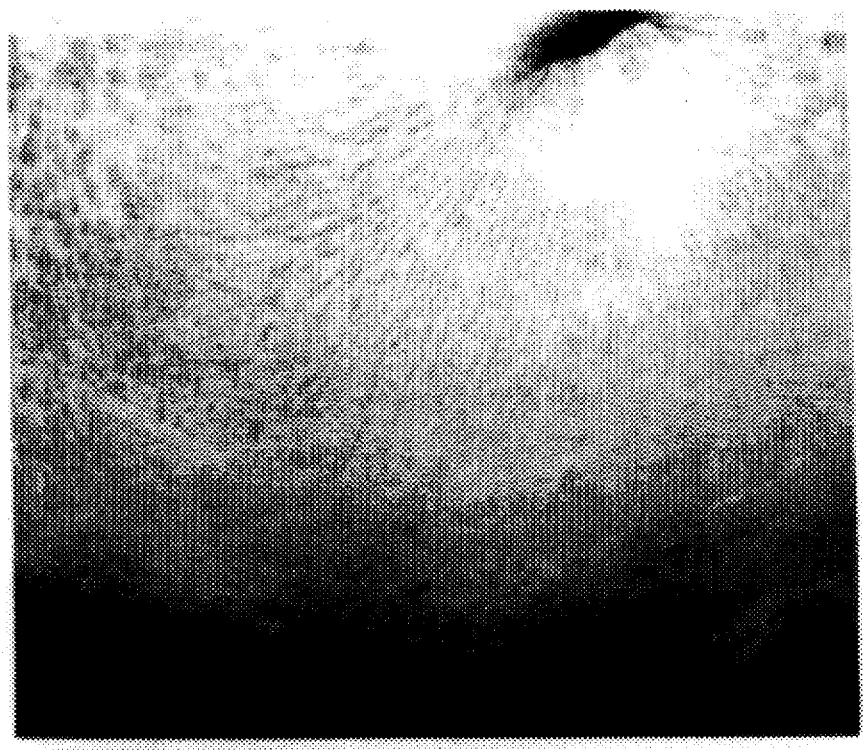

In FIG. 10A, an anterolateral abdomen afflicted with psoriasis which has been treated with $B_{12}$AC-Poly-R2 is shown on the right. This can be compared with the left side of the photograph which shows an untreated area. The area in 10A was treated once daily for 7 days with $B_{12}$AC-Poly-2. By comparing the two sides of the photograph, it can be seen that the treated psoriatic lesions appear less scaly, less thick and smoother. Stretch marks of the surrounding and underlying skin are also more visible through the thinner plaques of the treated region. In 10B a close-up of an untreated psoriatic plaque is set forth, showing thick, silvery scales with underlying red inflamed base. In 10C a treated area of the abdomen is shown. After 7 days of once daily treatment, less scaling and smoothening of lesions was evident. Again, normal skin markings are visible through the thinner plaques. The redness is a stain from the application of the $B_{12}$AC-Poly-R2.

FIG. 11 compares an untreated 11A and a treated 11B left lateral thigh afflicted with psoriasis. The skin was treated with $B_{12}$AC-Poly-R2 twice daily for 7 days. As can be seen in the figure, the treated area appeared smoother and the plaques were thinner. The untreated area had thick papulosquamous plaques showing silvery scales and a red inflamed base.

Figure 12A:
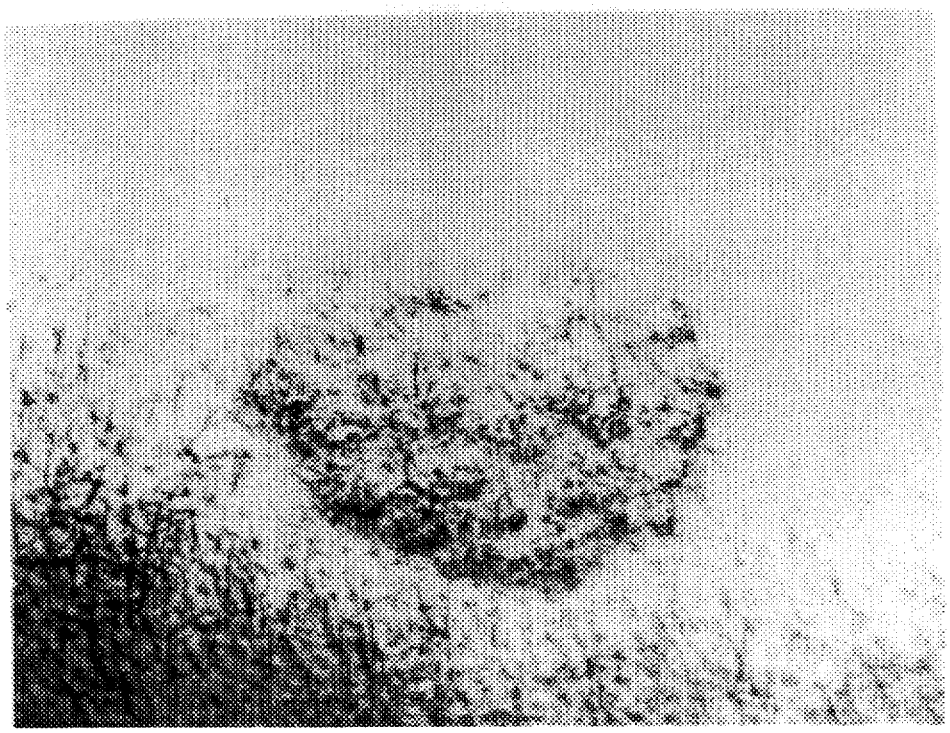
Figure 12B:
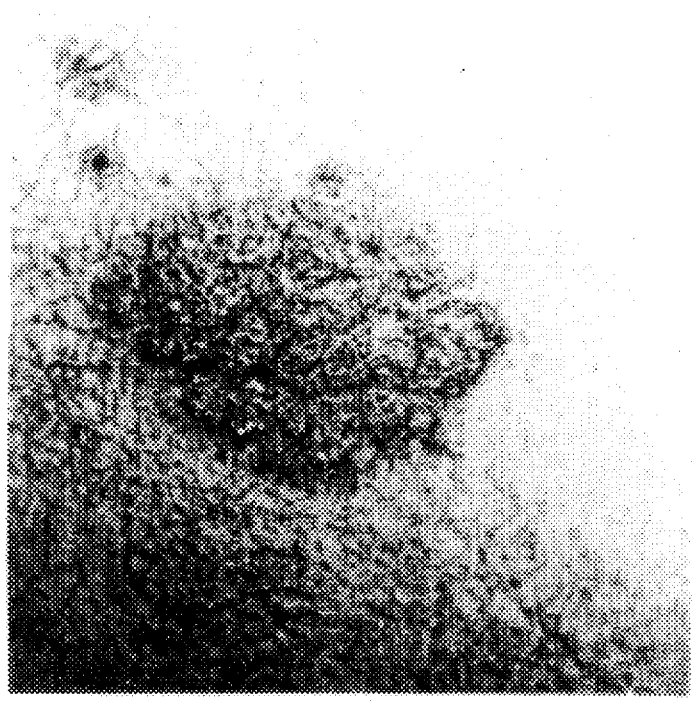
Figure 12C:
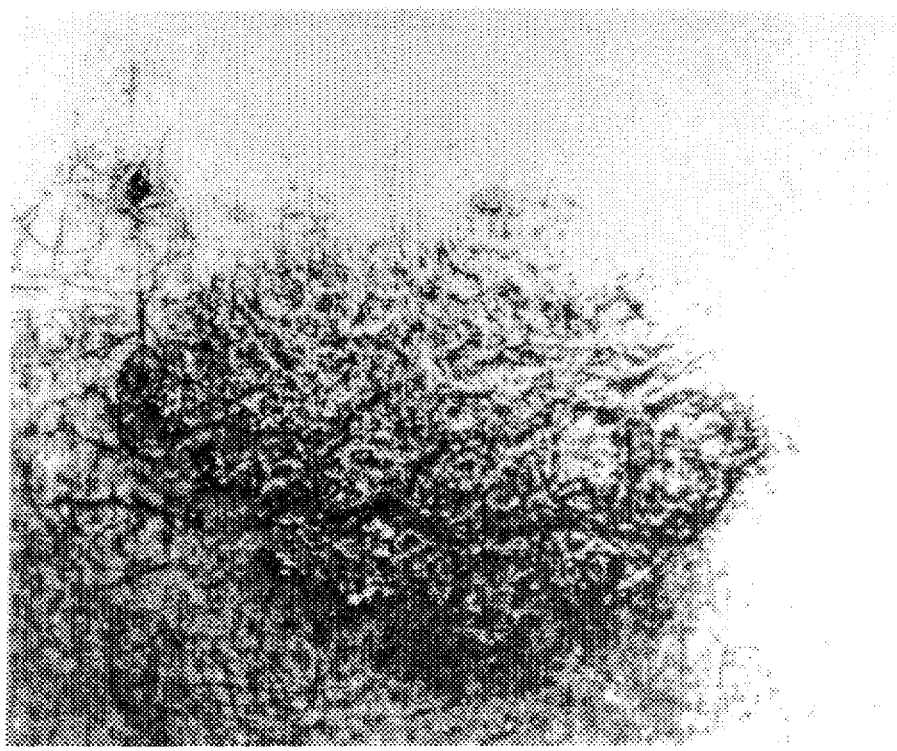

FIG. 12A illustrates a left lateral thigh with psoriatic plaque prior to treatment. FIG. 12B illustrates the same lesion after twice daily treatment with $B_{12}$AC-Poly-R2 for a 2 week time period. As can be seen by comparison of the figures, the treated lesions appeared flatter and contracted centrally with an overall diminution in size. In addition, overlying yellowish "scabs" were evident, giving an impression of dryness. Superficial fissuring may signify the drying effect and/or contraction of sections of the lesion. One smaller lesion in the upper right quadrant remained unchanged. FIG. 12C shows the same area as in 12B at a higher magnification. The above-described features are even more evident at the higher magnification. In addition, the small lesion in the upper left quadrant was superficially eroded and appeared necrotic.

Figure 13A:
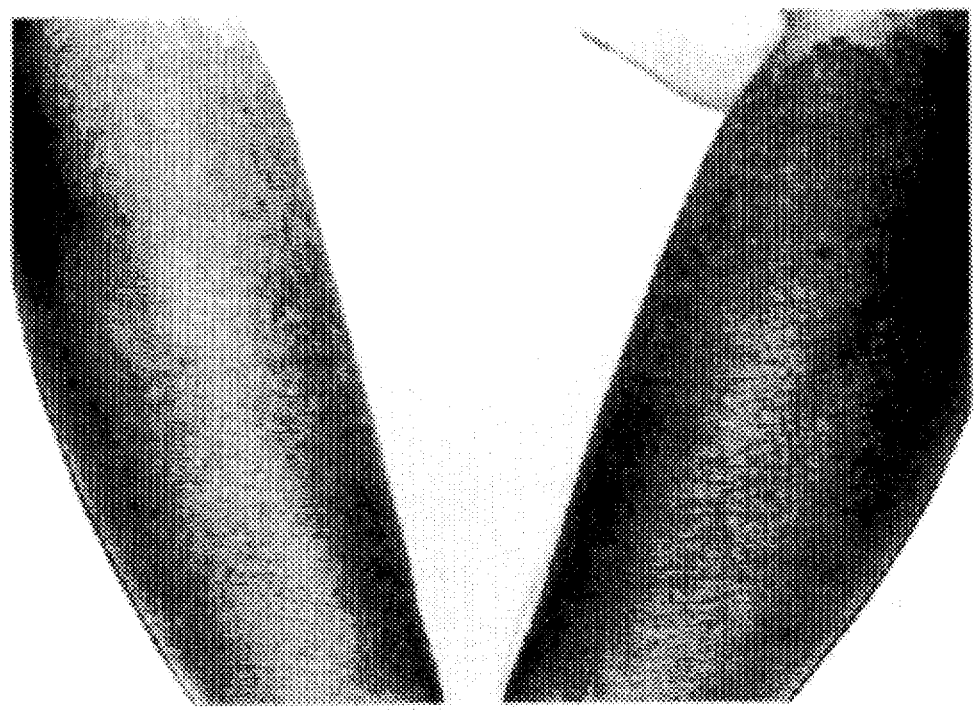
Figure 13B:
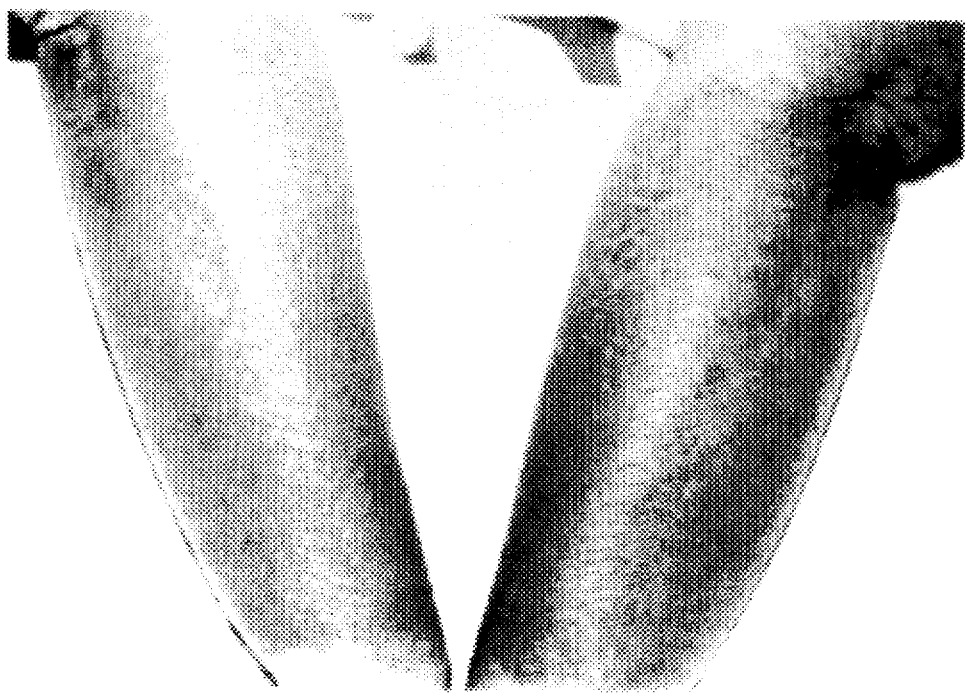

FIG. 13A illustrates a dorsolateral view of forearms encased in thick plaques of psoriasis prior to treatment with $B_{12}$AC-Poly-R2. FIG. 13B shows the same forearms one week later after treatment twice daily with $B_{12}$AC-Poly-R2 of the left forearm. The right forearm was untreated. By comparison of the two forearms, it can be seen that the treated areas on the left forearm showed less scaling with smoothening and thinning of the lesions. In particular, improvement was noted on the area below the left elbow.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A method of treatment of psoriasis comprising administering a complex of palladium or a palladium salt and lipoic acid in an amount effective for reduction of maculopapules associated with psoriasis to a patient in need of such treatment.

2. The method of claim 1 wherein the palladium-lipoic acid complex further comprises thiamine or a thiamine salt.

3. The method of claim 2 wherein the thiamine salt of the palladium-lipoic acid complex further comprises a synthetic cofactor of vitamin $B_{12}$ (cyanocobalamin).

4. The method of claim 3 wherein a parenteral route of administration is employed.

5. The method of claim 4 wherein the parenteral route of administration employed is a topical route of administration.

6. The method of claim 5 wherein a palladium-lipoic acid-synthetic cofactor of $B_{12}$ complex is topically administered to the patient at a dosage of between about 5 and about 80 ml daily of a 0.04M solution of the thiamine salt of a palladium-lipoic acid complex for at least about 5 days.

7. The method of claim 1 wherein the psoriasis comprises psoriasis vulgaris.

8. The method of claim 1 wherein the lipoic acid comprises a lipoic acid derivative having a carbon chain of between 2 and 20 carbon atoms, or a lipoic acid derivative having a side group or groups selected from the group consisting of carboxyl, sulfur and amine.

9. The method of claim 1 wherein the palladium salt is selected from the group consisting of palladium chloride, palladium bromide, palladium iodide, palladium nitrate, palladium oxide and palladium sulfide.

10. The method of claim 2 wherein the thiamine salt is selected from the group consisting of thiamine hydrochloride, thiamine nitrate, thiamine phosphate and thiamine pyrophosphate.

\* \* \* \* \*